United States Patent
Frangioni et al.

(10) Patent No.: US 9,023,611 B2
(45) Date of Patent: May 5, 2015

(54) CHARGED-BALANCED IMAGING AGENTS

(75) Inventors: John V. Frangioni, Wayland, MA (US); Maged M. Henary, Lawrenceville, GA (US)

(73) Assignees: Beth Israel Deaconess Medical Center, Boston, MA (US); Georgia State University Research Foundation, Inc., Atlanta, GA (US)

( * ) Notice: Subject to any disclaimer, the term of this patent is extended or adjusted under 35 U.S.C. 154(b) by 716 days.

(21) Appl. No.: 13/148,137

(22) PCT Filed: Feb. 5, 2010

(86) PCT No.: PCT/US2010/023305
§ 371 (c)(1),
(2), (4) Date: Oct. 13, 2011

(87) PCT Pub. No.: WO2010/091243
PCT Pub. Date: Aug. 12, 2010

(65) Prior Publication Data
US 2012/0028291 A1 Feb. 2, 2012

Related U.S. Application Data

(60) Provisional application No. 61/150,522, filed on Feb. 6, 2009.

(51) Int. Cl.
| | | |
|---|---|---|
| C12Q 1/02 | (2006.01) | |
| C07D 209/02 | (2006.01) | |
| A61K 49/00 | (2006.01) | |
| C07D 255/02 | (2006.01) | |
| A61B 6/00 | (2006.01) | |
| C09B 23/01 | (2006.01) | |
| C09B 23/08 | (2006.01) | |

(52) U.S. Cl.
CPC .............. A61K 49/0032 (2013.01); C12Q 1/02 (2013.01); C07D 209/02 (2013.01); C07D 255/02 (2013.01); A61B 6/00 (2013.01); C09B 23/0066 (2013.01); C09B 23/086 (2013.01)

(58) Field of Classification Search
CPC ............ A61K 49/0032; C09B 23/086; C09B 23/0066; C07D 209/02; C07D 255/02; A61B 6/00; C12Q 1/02
USPC .............................. 435/29; 548/455; 600/431
See application file for complete search history.

(56) References Cited

U.S. PATENT DOCUMENTS

| | | | |
|---|---|---|---|
| 6,875,886 B2 | 4/2005 | Frangioni | |
| 2006/0063834 A1 | 3/2006 | Frangioni et al. | |
| 2006/0147379 A1* | 7/2006 | Bornhop et al. | 424/9.6 |
| 2006/0280688 A1* | 12/2006 | Kovar et al. | 424/9.6 |
| 2007/0161116 A1* | 7/2007 | Copse | 436/172 |
| 2008/0044811 A1 | 2/2008 | Haugland et al. | |
| 2011/0262354 A1* | 10/2011 | Chung et al. | 424/9.1 |

FOREIGN PATENT DOCUMENTS

| | | |
|---|---|---|
| WO | WO-01/90253 A1 | 11/2001 |
| WO | WO-03/082988 A1 | 10/2003 |
| WO | WO-2006/020947 A2 | 2/2006 |
| WO | WO-2007/005222 A2 | 1/2007 |
| WO | WO-2007/036996 A1 | 4/2007 |
| WO | WO-2008/015415 A2 | 2/2008 |
| WO | WO-2008/017074 A2 | 2/2008 |
| WO | WO-2009/006443 A1 | 1/2009 |
| WO | WO 2009014513 A1 * | 1/2009 |

OTHER PUBLICATIONS

Hilderbrand et al. Bioconjugate Chemistry (2005) 16: 1275-1281.*
Banerjee, S.R *J. Med. Chem.* 2008, 51:4504-17.
Chandn, S.S., et al. *Cancer Biol. Ther.*, 2008, 7:974-82.
Chen, Y., et al. *J. Med. Chem*, 2008, 51:7933-43.
De Grand, A.M. and J.V. Frangioni, *An operational near-infrared fluorescence imaging system prototype for large animal surgery.* Technol Cancer Res Treat, 2003. 2:553-562.
Foss, C.A. et al. *Clin. Cancer. Res.*, 2005, 11:4022-8.
Humblet, V. et al. *Mol. Imaging*, 2005, 4:448-62.
Lee, H. et al. J. Org <http://J.Org>. Chem. (2006) 71, 7862-7865.
Maison, W., J.V. Frangioni, and N. Pannier, Synthesis of rigid multivalent scaffolds based on adamantane.Org <http://adamantane.Org> Lett, 2004. 6:4567-9.
Makin, S.M. et al. *Journal of Organic Chemistry of the USSR* (1977) 13(6), part 1, 1093-1096.
Mease, R.C., et al. *Clin. Cancer Res.*, 2008, 14:3036-43.
Misra P. et al. J. *Nucl. Med.* 2007, 48: 1379-89.
Mojzych, M. et al. "Synthesis of Cyanine Dyes" Top. Heterocycl. Chem. (2008) 14:1-9.

(Continued)

*Primary Examiner* — Susan Hanley
(74) *Attorney, Agent, or Firm* — Mintz Levin Cohn Ferris Glovsky and Popeo, P.C.; Peter F. Corless

(57) ABSTRACT

The present invention relates to compositions and methods of optically imaging tissues or cells using imaging agents have in vivo properties that result in signal-to-background ratios of at least about 1:1. TL is a targeting ligand and n is −1, 0 or +1.

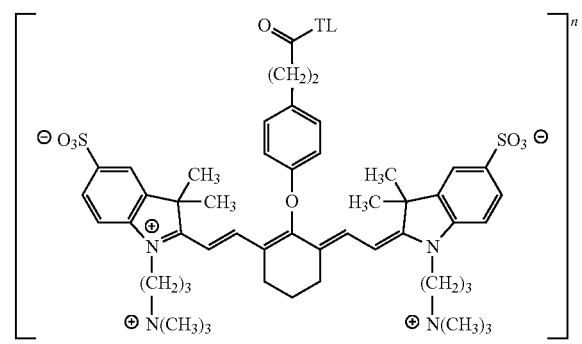

7 Claims, 9 Drawing Sheets

(56) References Cited

OTHER PUBLICATIONS

Nakayama, A., F. del Monte, R.J. Hajjar, and J.V. Frangioni, *Functional near-infrared fluorescence imaging for cardiac surgery and targeted gene therapy*. Molecular Imaging, 2002. 1:365-377.
Narayanan, N. et al. J. Org <http://J.Org>. Chem. (1995), 60(8), 2391-2395.
Nasr, K., N. Pannier, J.V. Frangioni, and W. Maison, *Rigid Multivalent Scaffolds Based on Adamantane*. J Org Chem, 2008.
Strekowski, L. et al. J. Org <http://J.Org>. Chem. (1992) 57, 4578-4580.
Strekowski, L. et al. *Synthetic Communications* (1992), 22(17), 2593-2598.
Tanaka, E., H.S. Choi, H. Fujii, M.G. Bawendi, and J.V. Frangioni, *Image-guided oncologic surgery using invisible light: completed preclinical development for sentinel lymph node mapping*. Ann Surg Oncol, 2006. 13: 1671-81.
Zaheer et al., *Nature Biotechnology*, 19, 1148-1154 (2001).

\* cited by examiner

CHARGED-BALANCED IMAGING AGENTS

CROSS REFERENCE TO RELATED APPLICATIONS

This application is a National Stage of International Application No. PCT/US2010/023305, filed Feb. 5, 2010, which claims the benefit of U.S. Application No. 61/150,522, filed Feb. 6, 2009.

FEDERALLY SPONSORED RESEARCH OR DEVELOPMENT

This invention was made with Government support under Grant No. R01-CA-115296 awarded by the National Institutes of Health. The Government has certain rights in the invention.

FIELD OF THE INVENTION

The present invention relates to methods of optically imaging tissues or cells using imaging agents having desirable in vivo properties that result in improved signal-to-background ratio.

BACKGROUND OF THE INVENTION

Near infrared (NIR) fluorescence has potential importance in the medical field, particularly in diagnostics and image-guided surgery. However, the availability of suitable fluorophores as imaging agents has been a primary hindrance. To be clinically viable, the ideal NIR fluorophore should have both good optical properties and superior in vivo properties with respect to solubility, biodistribution, and clearance. Most current fluorophores contemplated for use as imaging agents fail in connection with their in vivo properties. For example, known fluorophores tend to clear through the liver, which results in undesirable fluorescence throughout the gastrointestinal tract. And in some cases, known fluorophores suffer from significant non-specific background uptake in normal tissues, resulting in a low signal-to-background ratio. Accordingly, there is a current need for new and improved NIR fluorescent imaging agents, particularly those that can equilibrate rapidly between the intravascular and extravascular spaces and are cleared efficiently by renal filtration. The imaging agents of the invention are directed toward these and other needs.

SUMMARY OF THE INVENTION

The invention is based, at least in part, on the discovery that if one balances, or almost balances, the overall charge on an imaging agent molecule, then the resulting charge-balanced molecule has improved in vivo properties that lead to superior clinical imaging characteristics.

In one aspect, the present invention provides methods of imaging tissue or cells, the methods including (a) contacting the tissue or cells with an imaging agent comprising a dye or conjugate thereof, the conjugate comprising a targeting ligand attached to the dye, wherein the dye or conjugate has a net charge of +1, 0, or −1 and comprises one or more ionic groups; (b) irradiating the tissue or cells at a wavelength absorbed by the dye or conjugate; (c) detecting an optical signal from the irradiated tissue or cells, wherein the signal-to-background ratio of the detected optical signal is at least about 1.1, thereby imaging the tissue or cells.

The present invention further provides methods of preparing a dye for imaging tissue or cells, the method including (a) selecting a dye having peak absorption at about 500 nm to about 850 nm and peak fluorescent emission at about 550 nm to about 875 nm; (b) optionally modifying the dye to include a linking group; and (c) modifying the dye, and optionally the linking group, to include one or more ionic groups to achieve a solubility of the dye of at least about 10 µM in 10 mM HEPES solution at pH 7.4; wherein the one or more ionic groups are selected so that the net charge of the dye is +1, 0, or −1, and wherein the signal-to-background ratio of fluorescent emission detected from the dye compound while imaging is at least about 1.1.

In another aspect, the present invention further provides methods of preparing a conjugate for imaging tissue or cells, wherein the conjugate includes a dye and a targeting ligand. These methods include (a) selecting a dye having peak absorption at about 500 nm to about 850 nm and peak fluorescent emission at about 550 nm to about 875 nm; (b) optionally modifying the dye to include a linking group; (c) modifying the dye and optionally the linking group to include one or more ionic groups to achieve a solubility of at least about 10 µM in 10 mM HEPES solution at pH 7.4; and (d) conjugating the targeting ligand to the dye optionally through the linking group to form the conjugate, wherein the targeting ligand and the one or more ionic groups are selected so that the net charge of the conjugate is +1, 0, or −1, and wherein the signal-to-background ratio of fluorescent emission detected from the conjugate while imaging is at least about 1.1.

In addition, the present invention includes imaging agents for imaging tissue or cells, wherein the imaging agents include a conjugate which is characterized as having detectable fluorescence with a signal-to-background ratio of at least about 1.1, and wherein the conjugate has Formula VI:

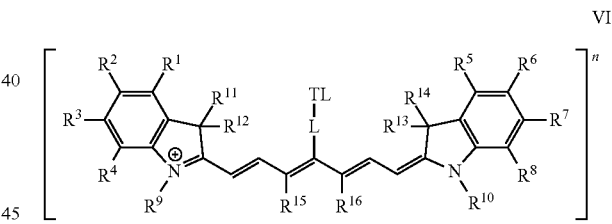

wherein constituent variables are defined herein.

The present invention further provides a dye comprising a molecule or ion of Formula VIII:

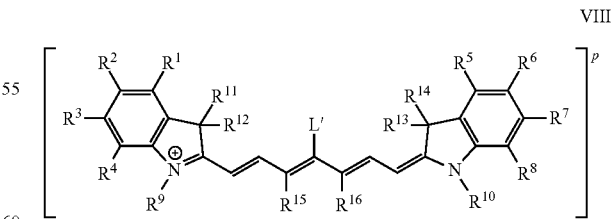

wherein constituent variables are defined herein.

The charge-balanced imaging agents of the invention are particularly advantageous because their behavior in vivo is believed to contribute to superior optical imaging properties. More specifically, the charge-balancing is believed to impart good biodistribution and clearance properties to the agents, and reduce undesirable non-specific binding. These in vivo properties help improve the signal-to-background ratio of imaged tissues, leading to higher resolution imaging.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
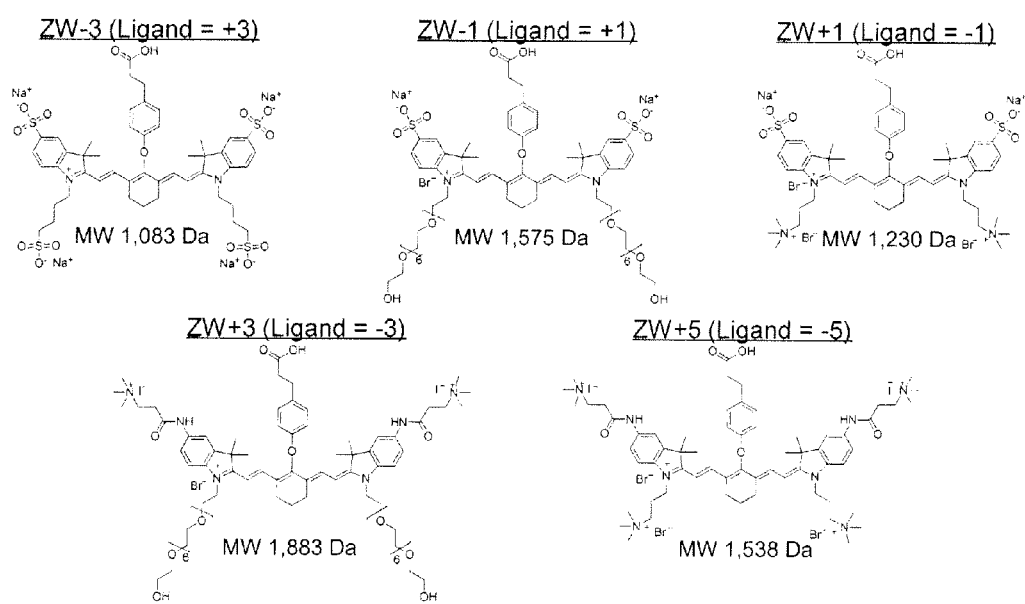
FIG. 1 a representation of dye molecules having a range of net charges.

The present disclosure relates, inter alia, to imaging agents that are composed of a dye molecule optionally conjugated to a targeting ligand through a linking group. The imaging agents described herein are useful in, for example, the detection of abnormal or diseased biological tissues and cells. The conjugates are particularly useful for imaging whole organisms, because they have improved in vivo behavior, such as low non-specific binding to non-targeted tissues, resulting in an improved signal-to-background ratio in connection with the detected optical signal. It is believed that these improved in vivo properties result from the balancing of formal charges on the conjugate, rendering a "charge-balanced" molecule having a net charge that is neutral or close to neutral.

Imaging Methods

The new methods of imaging tissue or cells include the following basic steps:

(a) contacting the tissue or cells with an imaging agent comprising a dye or conjugate thereof, the conjugate comprising a targeting ligand attached to the dye, wherein the dye or conjugate has a net charge of +1, 0, or −1 and comprises one or more ionic groups;

(b) irradiating the tissue or cells at a wavelength absorbed by the dye or conjugate;

(c) detecting an optical signal from the irradiated tissue or cells, wherein the signal-to-background ratio of the detected optical signal is at least about 1.1, thereby imaging the tissue or cells.

The imaging agents described herein are substances or molecules that can be used to image tissues or cells, such as those of a living organism, for purposes of diagnosis, therapy, image-guided surgery, and the like. In some embodiments, the organism is a mammal, such as a human.

The imaging agents generally contain a dye that is capable of absorption of electromagnetic radiation, typically in the ultraviolet (UV), visible, or near infrared (NIR) range. The imaging agent can also be capable fluorescent emission, such as in the visible or NIR range. The optical signal detected from the dye or conjugate can be, for example, absorption or fluorescent emission. In some embodiments, fluorescent emission from the dye is the primary optical signal detected for imaging purposes. In some embodiments, the dye has a peak absorbance at about 525 nm to about 850 nm, at about 550 nm to about 825 nm, about 600 nm to about 825 nm, about 700 nm to about 825 nm, or at about 750 nm to about 825 nm. In some embodiments, the dye has a peak fluorescent emission at about 700 nm to 875 nm, about 725 to about 850 nm, about 750 to about 850 nm, or about 775 to about 850 nm.

Suitable dyes for imaging by fluorescent emission include the class of cyanine dyes which are cationic molecules where two cyclic groups are linked through a methine or polymethine bridge. See the following references for examples of various cyanine dye derivatives: Mojzych, M. et al. "Synthesis of Cyanine Dyes" Top. Heterocycl. Chem. (2008) 14:1-9; Sysmex Journal International (1999), Vol. 9, No. 2, pg 185 (appendix); Strekowski, L. et al. Synthetic Communications (1992), 22(17), 2593-2598; Strekowski, L. et al. J. Org. Chem. (1992) 57, 4578-4580; Narayanan, N. et al. J. Org. Chem. (1995), 60(8), 2391-2395; Makin, S. M. et al. Journal of Organic Chemistry of the USSR (1977) 13 (6), part 1, 1093-1096; Lee, H. et al. J. Org. Chem. (2006) 71, 7862-7865, WO 2009/006443, WO 2008/015415, WO 2007/136996, WO 2007/005222, WO 2003/082988, WO 2001/090253, U.S. Ser. No. 12/376,243 (filed Feb. 3, 2009), and U.S. Ser. No. 12/376,225 (filed Feb. 3, 2009), each of which is incorporated herein by reference in its entirety. Example dyes and their conjugates suitable for use in the present imaging methods are described herein.

The imaging agents can include conjugates, which refers to a dye which is conjugated to a targeting ligand. The "targeting ligand" is a moiety that binds with some specificity or selectivity to a particular tissue or biological target. The tissue or biological target can include normal tissues as well as abnormal or diseased tissues. Targeting ligands can be selected from specific proteins, protein fragments, peptides, antibodies, carbohydrates, or antigens described, e.g., in Frangioni et al. in "Modified PSMA Ligands and Uses Related Thereto," WO 02/098885, filed on Feb. 7, 2002 (now issued as U.S. Pat. No. 6,875,886).

An example targeting ligand is the cRGD peptide, which selectively binds to the biological target $\alpha_v\beta_3$ integrin. It is known that this integrin is overexpressed by various tumors, and thus, these RGD targeting peptides enable the dyes to preferentially label tumors that overexpress these integrins. Other targeting ligands include melanocyte stimulating hormone (MSH), which binds to melanoma cells; or bombesin, somatostatin, or Sandostatin™ (synthetic), which target somatostatin receptors. Other targeting ligands include "KUE" and other small molecules, which selectively bind to the biological target prostate-specific membrane antigen (PSMA) (See, Humblet, V. et al. *Mol. Imaging*, 2005, 4: 448-62; Misra P. et al. *J. Nucl. Med.* 2007, 48: 1379-89; Chen, Y., et al. *J. Med. Chem.*, 2008, 51: 7933-43; Chandran, S. S., et al. *Cancer Biol. Ther.*, 2008, 7:974-82; Banerjee, S. R., *J. Med. Chem.* 2008, 51: 4504-17; Mease, R. C., et al. *Clin. Cancer Res.*, 2008, 14:3036-43; Foss, C. A. et al. *Clin. Cancer. Res.*, 2005, 11:4022-8, each of which is incorporated herein by reference in its entirety). Examples of suitable targeting ligands are described elsewhere herein.

The imaging agents are generally "charge-balanced," unless otherwise specified, which refers to having a net overall charge of zero, or close to zero, such as +1 or −1. Charge-balancing occurs when negatively charged substituents on the imaging agent are countered by the presence of an equal number, or close to an equal number, of positively charged substituents on the same molecule, and vice versa. In some embodiment, the net charge is 0 or +1. In some embodiments, the net charge is 0. In some embodiments, the net charge is +1. In further embodiments, the net charge is −1. The value "n" in the formulae provided herein represents net charge.

The imaging agents described herein generally have improved "signal-to-background ratio" (SBR) compared to presently known fluorescent imaging agents. The improvement in SBR is believed to be a result of improved in vivo properties due to "charge-balancing." SBR is a measure of the intensity of the fluorescent signal obtained from a target (peak signal) over the measure of the intensity of the fluorescent signal obtained nearby the target (background signal), the target being the tissues or cells targeted by the imaging agent. SBR measurements can be readily obtained through routine measurement procedures. For fluorescent imaging systems, and other optical-type systems, digital images recording optical signals of the target facilitate SBR measurement. Higher SBR values are more desirable, resulting in greater resolution of the imaged tissues. In some embodiments, the imaging agents achieve an SBR of at least about 1.1 (i.e., peak signal is at least 10% over background). In further embodiments, the imaging agents achieve an SBR of at least about 1.2, at least about 1.3, at least about 1.4, at least about 1.5, at least about 1.6, at least about 1.7, at least about 1.8, at least about 1.9, or at least about 2.0. In yet further embodiments, the imaging agents achieve an SBR of about 1.1 to about 50, about 1.5 to about 30, about 2.0 to about 20, about 2.0 to about 5.0, or about 5.0 to about 10.

The imaging agents generally include one or more ionic groups. In some embodiments, the imaging agents include two or more, three or more, four or more, or five or more ionic groups. Ionic groups serve to increase solubility of the generally hydrophobic dye portions of the imaging agent, thus, improving biodistribution. The ionic groups can be located on any portion of the imaging agent, such as the dye portion, the targeting ligand, or both.

The term "ionic group" refers to a moiety comprising one or more charged substituents. The "charged substituent" is a functional group that is generally anionic or cationic in substantially neutral aqueous conditions (e.g. a pH of about 6.5 to 8.0, or preferably about physiological pH (7.4)). Examples of charged anionic substituents include anions of inorganic and organic acids such as sulfonate ($-SO_3^{1-}$), supinate, carboxylate, phosphinate, phosphonate, phosphate, and esters (such as alkyl esters) thereof. In some embodiments, the charged substituent is sulfonate. Examples of charged cationic substituents include quaternary amines ($-NR_3^+$), where R is independently selected from $C_{1-6}$ alkyl, aryl, and arylalkyl. Other charged cationic substituents include protonated primary, secondary, and tertiary amines, and well as guanidinium. In some embodiments, the charged substituent is $-N(CH_3)_3^+$. Further examples of ionic groups are described infra.

The imaging agents described herein generally have good solubility in substantially neutral aqueous media, and in particular, blood and blood serum. In some embodiments, the imaging agent has a solubility in 10 mM HEPES solution, pH 7.4, of at least about 10 μm. In further embodiments, the imaging agent has a solubility in 10 mM HEPES solution, pH 7.4, of at least about 15 μM, at least about 20 μM, at least about 25 μM, at least about 30 μM, at least about 40 μM, or at least about 50 μM.

The imaging agents can be neutral molecules or salts. For example, if the dye or dye conjugate is charged, the imaging agent can be or contain a salt or acid (or combination thereof) of the dye or dye conjugate. For positively charged dyes or conjugates, suitable counter ions include anions such as fluoride, chloride, bromide, iodide, acetate, perchlorate, $PF_6^-$, and the like. For negatively charged dyes or conjugates, suitable counterions include cations such as $Na^+$, $K^+$, and quaternary amines.

The imaging agents of the invention can be administered by any suitable technique, including both enteral and parenteral methods. In some embodiments, the imaging agents can be formulated into pharmaceutically acceptable formulations and administered intravenously to an organism for imaging. The dosed organism can be imaged using, for example, a FLARE™ Image-Guided Surgery System, which is a continuous-wave (CW) intraoperative imaging system that is capable of simultaneous, real-time acquisition and display of color video (i.e., surgical anatomy) and two channels of invisible NIR fluorescent (700 nm and 800 nm) light. The imaging system can irradiate the dosed organism with radiation absorbed by the imaging agent, and detect optical signals, such as NIR fluorescence, eminating from the targeted portions of the organism containing the imaging agent. The detected signals can be recorded and analyzed by obtaining digital images or video of the subject organism, thereby facilitating diagnostic procedures and image-guided medical techniques.

Dyes and Conjugates

In some embodiments, the dyes or conjugates of the invention can have Formula I:

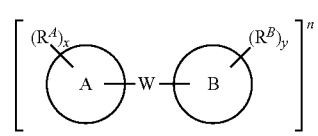

wherein:

n is +1, 0, or −1;

W is a $C_1$ methine or a $C_{2-13}$ polymethine group optionally substituted with 1, 2, 3, or 4 substituents independently selected from $C_{1-6}$ alkyl, a reactive linking group, or a moiety comprising a linking group and a targeting ligand, wherein two substituents, together with the atoms to which they are attached and optionally one or more methine groups of W, optionally form a 5-, 6-, or 7-membered carbocycle or a 5-, 6-, or 7-membered heterocycle, wherein said carbocycle or heterocycle is optionally substituted with 1, 2, 3, 4, 5, or 6 substituents independently selected from an ionic group, a non-ionic oligomeric or polymeric solubilizing group, halo, $C_{1-6}$ alkyl, aryl, and heteroaryl;

Ring A and Ring B are independently selected from a monocyclic heterocycle, a bicyclic heterocycle, a tricyclic heterocycle, a monocyclic a carbocycle, a bicyclic carbocycle, and a tricylic carbocycle, wherein one of Rings A and B is optionally charged;

$R^A$ and $R^B$ are independently selected from H, an ionic group, a non-ionic oligomeric or polymeric solubilizing group, halo, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

x and y are independently selected from 0, 1, 2, 3, 4, 5, 6, 7, 8, 9, 10, and 11; wherein at least one $R^A$ and $R^B$ is present and is an ionic group.

In some embodiments, at least two of $R^A$ and $R^B$ are present and are ionic groups. In further embodiments, at least three of $R^A$ and $R^B$ are present and are ionic groups. In yet further embodiments, at least four of $R^A$ and $R^B$ are present and are ionic groups. In some embodiments, at least one ionic group is a cationic group. In further embodiments, at least two ionic groups are cationic groups.

In some embodiments, Ring A is selected from a monocyclic heterocycle, a bicyclic heterocycle, and a tricyclic heterocycle.

In some embodiments, Ring A is selected from a bicyclic heterocycle and a tricyclic heterocycle, wherein Ring A has a formal charge of +1.

In some embodiments, Ring A has the Formula:

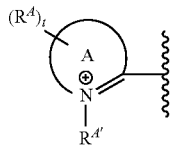

wherein:

Ring A is a bicyclic or tricyclic heterocycle;

$R^A$ is H, an ionic group, a non-ionic oligomeric or polymeric solubilizing group, halo, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

$R^{A'}$ is an ionic group, a non-ionic oligomeric or polymeric solubilizing group, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl; and t is 0, 1, 2, 3, 4, 5, 6, 7, 8, 9, or 10.

In some embodiments, the dye or conjugate has Formula II:

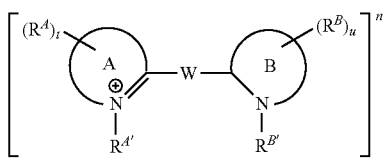

wherein:

n is +1, 0, or −1;

W is a $C_1$ methine or a $C_{2-13}$ polymethine group optionally substituted with 1, 2, 3, or 4 substituents independently selected from $C_{1-6}$ alkyl, a reactive linking group, or a moiety comprising a linking group and a targeting ligand, wherein two substituents, together with the atoms to which they are attached and optionally one or more methine groups of W, optionally form a 5-, 6-, or 7-membered carbocycle or a 5-, 6-, or 7-membered heterocycle, wherein said carbocycle or heterocycle is optionally substituted with 1, 2, 3, 4, 5, or 6 substituents independently selected from an ionic group, a non-ionic oligomeric or polymeric solubilizing group, halo, $C_{1-6}$ alkyl, aryl, and heteroaryl;

Ring A and Ring B are independently selected from monocyclic heterocycle, bicyclic heterocycle, and tricyclic heterocycle;

$R^A$ and $R^B$ are independently selected from H, an ionic group, a non-ionic oligomeric or polymeric solubilizing group, halo, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

$R^{A'}$ and $R^{B'}$ are independently selected from an ionic group, a non-ionic oligomeric or polymeric solubilizing group, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl; and u and t are independently selected from 0, 1, 2, 3, 4, 5, 6, 7, 8, 9, and 10; wherein at least one $R^A$, $R^B$, $R^{A'}$, $R^{B'}$ and $R^W$ is present and is an ionic group, and any other substituents are as defined infra and supra.

In some embodiments, at least two $R^A$, $R^B$, $R^{A'}$, $R^{B'}$, and $R^W$ are present and are ionic groups. In further embodiments, at least three $R^A$, $R^B$, $R^{A'}$, $R^{B'}$, and $R^W$ are present and are ionic groups. In yet further embodiments, at least four $R^A$, $R^B$, $R^{A'}$, $R^{B'}$, and $R^W$ are present and are ionic groups. In some embodiments, at least one $R^A$, $R^B$, $R^{A'}$, $R^{B'}$, and $R^W$ is a cationic group. In some embodiments, at least two $R^A$, $R^B$, $R^{A'}$, $R^{B'}$, and $R^W$ are cationic groups.

In some embodiments, the dye or conjugate has Formula III:

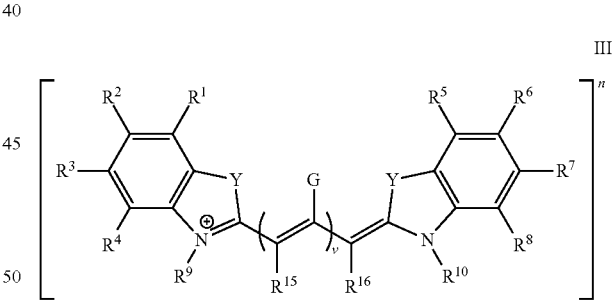

wherein:

G is independently selected from H, $C_{1-6}$ alkyl, a moiety comprising a linking group, and a moiety comprising a targeting ligand;

Y is O, S, $CR^{11}R^{12}$, $NR''$, $—CR^{11}=CR^{12}—$, or $—CR^{11}=N—$;

$R^1$, $R^2$, $R^3$, $R^4$, $R^5$, $R^6$, $R^7$, and $R^8$ are independently selected from H, an ionic group, a non-ionic oligomeric or polymeric solubilizing group, halo, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

or two adjacent $R^1$, $R^2$, $R^3$, $R^4$, $R^5$, $R^6$, $R^7$, and $R^8$ groups, together with the atoms to which they are attached, form a fused 5-7 membered aryl, heteroaryl, cycloalkyl, or heterocycloalkyl group, each optionally substituted with 1, 2, 3, 4, or 5 substituents independently selected from halo, cyano, nitro, and $C_{1-4}$ haloalkyl;

$R^9$, $R^{10}$, and R″ are independently selected from an ionic group, a non-ionic oligomeric or polymeric solubilizing group, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

$R^{11}$ and $R^{12}$ are independently selected from $C_{1-4}$ alkyl optionally substituted with 1, 2, or 3 halo;

$R^{15}$ and $R^{16}$ are independently selected from H and $C_{1-6}$ alkyl;

or $R^{15}$ and $R^{16}$, together with the atoms to which they are attached and optionally one or more —CH= moieties, form a 6-membered aryl or cycloalkyl group, each optionally substituted with 1, 2, 3, 4, 5, or 6 substituents independently selected from an ionic group, a non-ionic oligomeric or polymeric solubilizing group, halo, $C_{1-6}$ alkyl, aryl, and heteroaryl; and v is 0, 1, 2, 3, 4, or 5, wherein at least one of $R^1$, $R^2$, $R^3$, $R^4$, $R^5$, $R^6$, $R^7$, $R^8$, $R^9$, and $R^{10}$ is an ionic group, and any other substituents are as defined infra and supra.

In some embodiments, no more than one G is a moiety comprising a linking group or a moiety comprising a targeting ligand. In some embodiments, least two of $R^1$, $R^2$, $R^3$, $R^4$, $R^5$, $R^6$, $R^7$, $R^8$, $R^9$, and $R^{10}$ are ionic groups. In further embodiments, least three of $R^1$, $R^2$, $R^3$, $R^4$, $R^5$, $R^6$, $R^7$, $R^8$, $R^9$, and $R^{10}$ are ionic groups. In yet further embodiments, least four of $R^1$, $R^2$, $R^3$, $R^4$, $R^5$, $R^6$, $R^7$, $R^8$, $R^9$, and $R^{10}$ are ionic groups. In some embodiments, at least one of $R^1$, $R^2$, $R^3$, $R^4$, $R^5$, $R^6$, $R^7$, $R^8$, $R^9$, and $R^{10}$ is a cationic group. In further embodiments, at least two of $R^1$, $R^2$, $R^3$, $R^4$, $R^5$, $R^6$, $R^7$, $R^8$, $R^9$, and $R^{10}$ are cationic groups.

In some embodiments, the dye or conjugate has Formula IV:

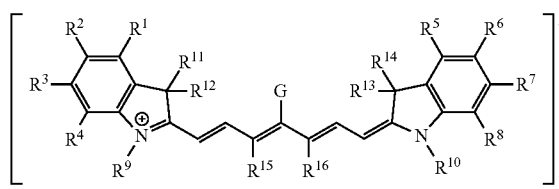

IV wherein $R^{13}$ and $R^{14}$ are independently selected from $C_{1-4}$ alkyl optionally substituted with 1, 2, or 3 halo, and any other substituents are as defined infra and supra In some embodiments, no more than one G is a moiety comprising a linking group or a moiety comprising a targeting ligand. In some embodiments, least two of $R^1$, $R^2$, $R^3$, $R^4$, $R^5$, $R^6$, $R^7$, $R^8$, $R^9$, and $R^{10}$ are ionic groups. In further embodiments, least three of $R^1$, $R^2$, $R^3$, $R^4$, $R^5$, $R^6$, $R^7$, $R^8$, $R^9$, and $R^{10}$ are ionic groups. In yet further embodiments, least four of $R^1$, $R^2$, $R^3$, $R^4$, $R^5$, $R^6$, $R^7$, $R^8$, $R^9$, and $R^{10}$ are ionic groups. In some embodiments, at least one of $R^1$, $R^2$, $R^3$, $R^4$, $R^5$, $R^6$, $R^7$, $R^8$, $R^9$, and $R^{10}$ is a cationic group. In further embodiments, at least two of $R^1$, $R^2$, $R^3$, $R^4$, $R^5$, $R^6$, $R^7$, $R^8$, $R^9$, and $R^{10}$ are cationic groups.

In some embodiments, the dye or conjugate has Formula V:

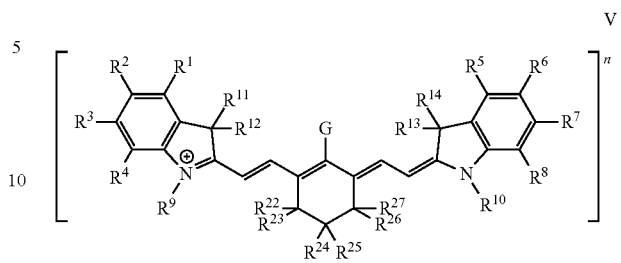

V wherein $R^{22}$, $R^{23}$, $R^{24}$, $R^{25}$, $R^{26}$, and $R^{27}$ are independently selected from an ionic group, a non-ionic oligomeric or polymeric solubilizing group, halo, $C_{1-6}$ alkyl, aryl, and heteroaryl, and any other substituents are as defined infra and supra.

In some embodiments, no more than one G is a moiety comprising a linking group or a moiety comprising a targeting ligand. In some embodiments, least two of $R^1$, $R^2$, $R^3$, $R^4$, $R^5$, $R^6$, $R^7$, $R^8$, $R^9$, and $R^{10}$ are ionic groups. In further embodiments, least three of $R^1$, $R^2$, $R^3$, $R^4$, $R^5$, $R^6$, $R^7$, $R^8$, $R^9$, and $R^{10}$ are ionic groups. In yet further embodiments, least four of $R^1$, $R^2$, $R^3$, $R^4$, $R^5$, $R^6$, $R^7$, $R^8$, $R^9$, and $R^{10}$ are ionic groups. In some embodiments, at least one of $R^1$, $R^2$, $R^3$, $R^4$, $R^5$, $R^6$, $R^7$, $R^8$, $R^9$, and $R^{10}$ is a cationic group. In further embodiments, at least two of $R^1$, $R^2$, $R^3$, $R^4$, $R^5$, $R^6$, $R^7$, $R^8$, $R^9$, and $R^{10}$ are cationic groups.

Conjugates

Suitable conjugates described herein can be characterized by Formula VI:

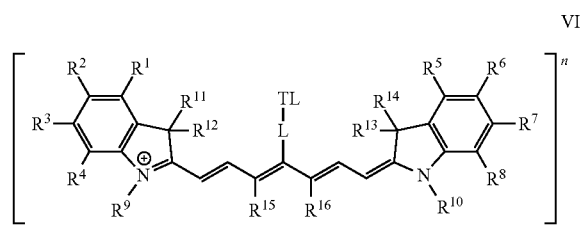

VI wherein:

TL is a targeting ligand comprising at least one binding moiety that binds to a biological target;

L is a linking moiety;

$R^1$, $R^2$, $R^3$, $R^4$, $R^5$, $R^6$, $R^7$, and $R^8$ are independently selected from H, an ionic group, a non-ionic oligomeric or polymeric solubilizing group, halo, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

or two adjacent $R^1$, $R^2$, $R^3$, $R^4$, $R^5$, $R^6$, $R^7$, and $R^8$ groups, together with the atoms to which they are attached, form a fused 5-7 membered aryl, heteroaryl, cycloalkyl, or heterocycloalkyl group, each optionally substituted with 1, 2, 3, 4, or 5 substituents independently selected from halo, cyano, nitro, and $C_{1-4}$ haloalkyl;

$R^9$ and $R^{10}$ are independently selected from an ionic group, a non-ionic oligomeric or polymeric solubilizing group, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

$R^{11}$, $R^{12}$, $R^{13}$, and $R^{14}$ are independently selected from $C_{1-4}$ alkyl optionally substituted with 1, 2, or 3 halo;

$R^{15}$ and $R^{16}$ are independently selected from H and $C_{1-6}$ alkyl;

or $R^{15}$ and $R^{16}$ together with the —CH=CH—CH= moiety which they span form a 6-membered aryl or cycloalkyl group, each optionally substituted with 1, 2, 3, or 4 substituents independently selected from an ionic group, a non-ionic oligomeric or polymeric solubilizing group, halo, $C_{1-6}$ alkyl, aryl, and heteroaryl; and n is +1, 0, or −1.

In some embodiments, at least one of $R^1$, $R^2$, $R^3$, $R^4$, $R^5$, $R^6$, $R^7$, $R^8$, $R^9$, and $R^{10}$ is an ionic group. In further embodiments, at least two of $R^1$, $R^2$, $R^3$, $R^4$, $R^5$, $R^6$, $R^7$, $R^8$, $R^9$, and $R^{10}$ are ionic groups. In yet further embodiments, at least three of $R^1$, $R^2$, $R^3$, $R^4$, $R^5$, $R^6$, $R^7$, $R^8$, $R^9$, and $R^{10}$ are ionic groups. In yet further embodiments, at least four of $R^1$, $R^2$, $R^3$, $R^4$, $R^5$, $R^6$, $R^7$, $R^8$, $R^9$, and $R^{10}$ are ionic groups.

In some embodiments, n is 0. In further embodiments, n is +1. In yet further embodiments, n is −1.

In some embodiments, the ionic group is independently selected from:

(a) a charged substituent; and (b) a $C_{1-20}$ alkyl group substituted with one or more charged substituents, and optionally substituted with 1, 2, 3, 4, 5, or 6 substituents independently selected from halo, cyano, nitro, and $C_{1-4}$ haloalkyl, wherein 0, 1, 2, 3, 4, 5, or 6 carbon atoms of the alkyl group are individually replaced with O, S, C(O), C(O)O, NR', C(O)NR', SO, $SO_2$, $SO_2$NR', wherein R' is H or $C_{1-6}$ alkyl, with the proviso that the replacement does not result in an unstable moiety.

In some embodiments, the charged substituent is selected from sulfonate or a quaternary amine of formula —$NR_3^+$, wherein R is independently selected from $C_{1-6}$ alkyl, aryl, and arylalkyl.

In some embodiments, the $C_{1-20}$ alkyl group substituted with one or more charged substituents has the Formula:

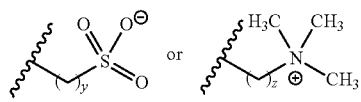

wherein y and z are independently selected from 1, 2, 3, 4, 5, 6, 7, and 8.

In some embodiments, the $C_{1-20}$ alkyl group substituted with one or more charged substituents is independently selected from:

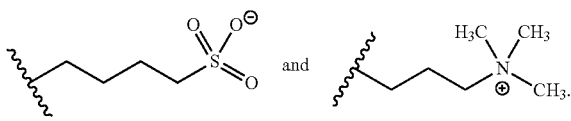

In some embodiments, the $C_{1-20}$ alkyl group substituted with one or more charged substituents is a Zwitterionic group. For example, the Zwitterionic group can comprise a sulfonate group and a quaternary amine of formula —$NR_3^+$, wherein R is independently selected from $C_{1-6}$ alkyl, aryl, and arylalkyl.

In some embodiments, $R^{11}$, $R^{12}$, $R^{13}$, and $R^{14}$ are each methyl.

In some embodiments, $R^{15}$ and $R^{16}$ together with the —C=C—C— moiety which they span form a 6-membered aryl or cycloalkyl group, each optionally substituted with 1, 2, 3, or 4 substituents independently selected from an ionic group, a non-ionic oligomeric or polymeric solubilizing group, halo, $C_{1-6}$ alkyl, aryl, and heteroaryl.

In some embodiments, $R^{15}$ and $R^{16}$ together form —$CH_2$—$CH_2$—$CH_2$—.

In some embodiments, L has the formula:

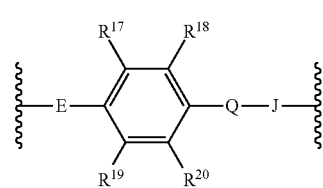

wherein:

E is absent, O or S;

Q is $(CH_2)_q$ or a non-ionic oligomeric or polymeric solubilizing moiety;

J is C(O), C(O)O, or C(O)NH;

$R^{17}$, $R^{18}$, $R^{19}$, and $R^{20}$ are independently selected from H, an ionic group, a non-ionic oligomeric or polymeric solubilizing moiety, halo, cyano, nitro, $C_{1-4}$ alkyl, $C_{1-4}$ alkoxy, and $C_{1-4}$ haloalkyl; and q is 0, 1, 2, 3, 4, 5, 6, 7, or 8.

In some embodiments, the conjugate has Formula VII:

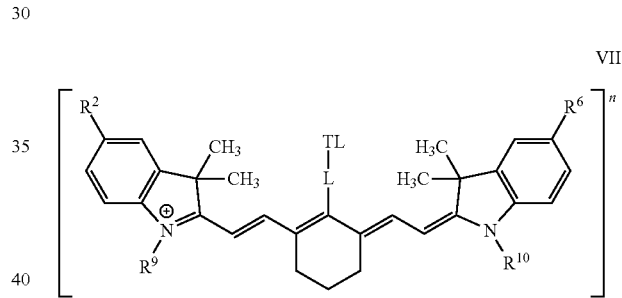

wherein the substituents are defined supra and infra, and wherein at least one of $R^2$, $R^6$, $R^9$, and $R^{10}$ is an ionic group. In some embodiments, n is +1. In further embodiments, two of $R^2$, $R^6$, $R^9$, and $R^{10}$ are cationic groups. In yet further embodiments, two of $R^2$, $R^6$, $R^9$, and $R^{10}$ are cationic groups and two of $R^2$, $R^6$, $R^9$, and $R^{10}$ are anionic groups.

In some embodiments, the conjugate has the Formula VIII:

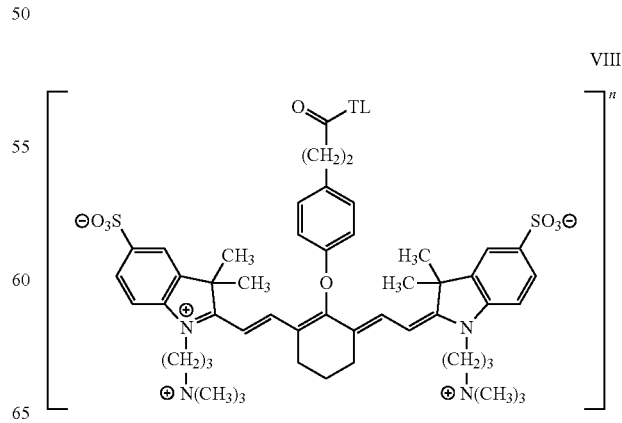

wherein:

n is 0, +1, or −1; and

TL is a targeting ligand.

Dyes

Suitable dyes described herein include a molecule or ion of Formula VIII:

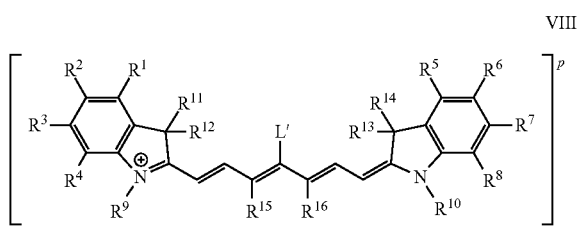

VIII wherein:

L' is a reactive linking group;

$R^1$, $R^2$, $R^3$, $R^4$, $R^5$, $R^6$, $R^7$, and $R^8$ are independently selected from H, an ionic group, a non-ionic oligomeric or polymeric solubilizing group, halo, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

or two adjacent $R^1$, $R^2$, $R^3$, $R^4$, $R^5$, $R^6$, $R^7$, or $R^8$ groups, together with the atoms to which they are attached, form a fused 5-7 membered aryl, heteroaryl, cycloalkyl, or heterocyclocalkyl group, each optionally substituted with 1, 2, 3, 4, or 5 substituents independently selected from halo, cyano, nitro, and $C_{1-4}$ haloalkyl;

$R^9$ and $R^{10}$ are independently selected from an ionic group, a non-ionic oligomeric or polymeric solubilizing group, $C_{1-6}$ alkyl, aryl, and heteroaryl, wherein said alkyl, aryl, and heteroaryl groups are optionally substituted with 1, 2, 3, 4, or 5 groups independently selected from halo, cyano, nitro, and $C_{1-4}$ haloalkyl;

$R^{11}$, $R^{12}$, $R^{13}$, and $R^{14}$ are independently selected from $C_{1-4}$ alkyl optionally substituted with 1, 2, or 3 halo;

$R^{15}$ and $R^{16}$ are independently selected from H and $C_{1-6}$ alkyl;

or $R^{15}$ and $R^{16}$ together with the —C=C—C— moiety which they span form a 6-membered aryl or cycloalkyl group, each optionally substituted with 1, 2, 3, or 4 substituents independently selected from an ionic group, a non-ionic oligomeric or polymeric solubilizing group, halo, $C_{1-6}$ alkyl, aryl, and heteroaryl; and p is −6, −5, −4, −3, −2, −1, 0, +1, +2, +3, +4, +5, or +6.

In some embodiments, at least one of $R^1$, $R^2$, $R^3$, $R^4$, $R^5$, $R^6$, $R^7$, $R^8$, $R^9$, and $R^{10}$ is an ionic group comprising at least one cationic substituent.

In some embodiments, L' comprises a —COOH group or a —C(O)O—NHS group.

In some embodiments, L' has the formula:

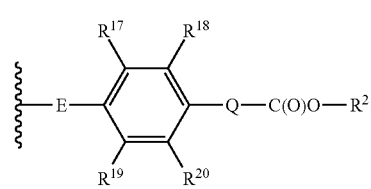

L' wherein:

E is absent, O or S;

Q is $(CH_2)_q$ or a non-ionic oligomeric or polymeric solubilizing moiety;

$R^{17}$, $R^{18}$, $R^{19}$, and $R^{20}$ are independently selected from H, an ionic group, a non-ionic oligomeric or polymeric solubilizing moiety, halo, cyano, nitro, $C_{1-4}$ alkyl, $C_{1-4}$ alkoxy, and $C_{1-4}$ haloalkyl;

$R^{21}$ is H or N-succinimidyl; and q is 0, 1, 2, 3, 4, 5, 6, 7, or 8.

In some embodiments, the dye comprises a molecule or ion of Formula IX:

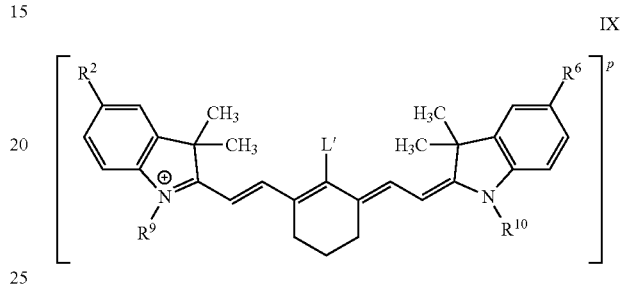

IX wherein the substituents are defined supra and infra, and wherein at least one of $R^2$, $R^6$, $R^9$, and $R^{10}$ is an ionic group comprising at least one cationic substituent.

In some embodiments, p is 0 or +1. In further embodiments, p is +1.

In some embodiments, at least two of $R^2$, $R^6$, $R^9$, and $R^{10}$ are ionic groups each comprising at least one cationic substituent.

In some embodiments, the dye compound has Formula X:

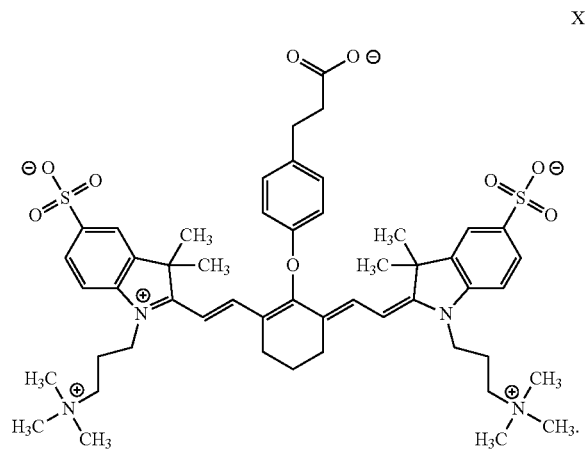 [SMILES: CC1(C)C(/C=C/C2=C(Oc3ccc(CCC(=O)[O-])cc3)C(=C/C=C3/N(CCC[N+](C)(C)C)c4ccc(S(=O)(=O)[O-])cc4C3(C)C)/CCC2)=[N+](CCC[N+](C)(C)C)c2ccc(S(=O)(=O)[O-])cc21]

X

DEFINITIONS AND ADDITIONAL EMBODIMENTS

As used herein, "targeting ligand" (TL) refers to any molecular entity that contains a binding moiety that binds with some specificity or selectivity to a biological target, and is the primary means for the conjugates of the invention to bind to specific tissues in an organism or sample. Targeting ligands can further include charged functional groups that would balance charge on a conjugated dye molecule. Generally, it is desired that the charge on the targeting ligand substantially neutralizes any charge on the dye compound such that the total net charge of the conjugate is −1, 0, or +1. In some embodiments, the total net charge is 0.

The targeting ligand can be covalently attached to the reactive linking group of a dye compound of the invention through standard coupling procedures. For example, the carboxyl or activated carboxyl group of the reactive linking group can react with a nucleophilic functionality on the targeting ligand, such as an amine or alkoxy derivative, to form an amide or ester linkage. Additional details for the conjugation of dyes can be found in WO 2008/017074 and in Frangioni et al. *Molecular Imaging*, Vol. 1(4), 354-364 (2002), each of which is incorporated herein by reference in its entirety.

The targeting ligand can further include a molecular scaffold moiety to which the binding moiety and other groups can attach. For example, the molecule scaffold can bear one or more of the following: (1) a moiety designed to react with the reactive linking group of the dye to form a covalent bond, (2) a charge balancing moiety, such as any of the ionic groups described herein, and (3) a moiety that binds to the biological target. An example of a molecular scaffold is an adamantane derivative, such as described in U.S. Pat. App. Pub. No. 2006/0063834, which is incorporated herein by reference in its entirety, and illustrates the preparation of a targeting ligand that incorporates an adamantane scaffold. Specifically, the adamantane core holds (1) an amino group capable of reacting with the dye compounds, (2) a charge-balancing moiety that will neutralize a negative charge on the dye molecule, and (3) two moieties that bind to the biological target PSMA. For a description moieties that bind to PSMA, see, Humblet, V. et al. *Mol. Imaging*, 2005, 4: 448-62; Misra P. et al. *J. Nucl. Med.* 2007, 48: 1379-89; Chen, Y., et al. *J. Med. Chem.*, 2008, 51: 7933-43; Chandran, S. S., et al. *Cancer Biol. Ther.*, 2008, 7:974-82; Banerjee, S. R., *J. Med. Chem.* 2008, 51: 4504-17; Mease, R. C., et al. *Clin. Cancer Res.*, 2008, 14:3036-43; Foss, C. A. et al. *Clin. Cancer. Res.*, 2005, 11:4022-8, each of which is incorporated herein by reference in its entirety.

As used herein, the term "contacting" refers to the bringing together of substances in physical contact such that the substances can interact with each other. For example, when an imaging agent is "contacted" with tissue or cells, the tissue or cells can interact with the imaging agent, for example, allowing the possibility of binding interactions between the agent and molecular components of the tissue or cells. "Contacting" is meant to include the administration of a substance such as an imaging agent of the invention to an organism. Administration can be, for example, oral or parenteral.

As used herein, the term "ionic group" refers to a moiety comprising one or more charged substituents. The "charged substituent" is a functional group that is generally anionic or cationic when in substantially neutral aqueous conditions (e.g. a pH of about 6.5 to 8.0 or about physiological pH (7.4)). As recited above, examples of charged anionic substituents include anions of inorganic and organic acids such as sulfonate ($-SO_3^{1-}$), sulfinate, carboxylate, phosphinate, phosphonate, phosphate, and esters (such as alkyl esters) thereof. In some embodiments, the charged substituent is sulfonate. Examples of charged cationic substituents include quaternary amines ($-NR_3^+$), where R is independently selected from $C_{1-6}$ alkyl, aryl, and arylalkyl. Other charged cationic substituents include protonated primary, secondary, and tertiary amines, and well as guanidinium. In some embodiments, the charged substituent is $-N(CH_3)_3^+$.

In some embodiments, the ionic group consists solely of a charged substituent. Example charged substituents include any of those mentioned above, including sulfonate and $-N(CH_3)_3^+$.

In further embodiments, the ionic group corresponds to a $C_{1-20}$ alkyl group substituted with one or more charged substituents, wherein the $C_{1-20}$ alkyl group is optionally further substituted with 1, 2, 3, 4, 5, or 6 substituents independently selected from halo, cyano, nitro, and $C_{1-4}$ haloalkyl, wherein 0, 1, 2, 3, 4, 5, or 6 carbon atoms of the alkyl group are individually replaced with O, S, C(O), C(O)O, NR', C(O)NR', SO, $SO_2$, $SO_2NR'$, wherein R' is H or $C_{1-6}$ alkyl, with the proviso that the replacement does not result in an unstable moiety (e.g., —O—O—, —O—S—, etc.).

Example ionic groups include groups of Formula:

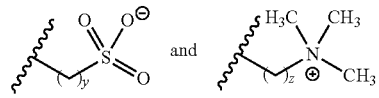

wherein y and z are independently selected from 0, 1, 2, 3, 4, 5, 6, 7, and 8. In some embodiments, y and z are independently selected from 1, 2, 3, 4, 5, 6, 7, and 8. In some embodiments, y and z are independently selected from 1, 2, 3, and 4. In some embodiments, y and z are 0.

Further example ionic groups include groups of Formula:

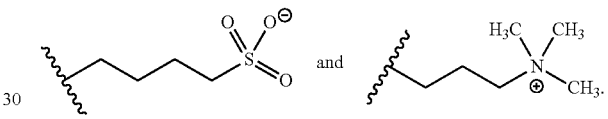

In some embodiments, the ionic group can contain two or more charged substituents. For example, the ionic group can include both an anionic and a cationic substituent, forming a "Zwitterionic group" (or "Zwitterion"). Zwitterionic groups can be particularly useful as substituents in the present invention because they incorporate additional formal charges in the conjugate yet do not impact net total charge, thereby facilitating charge-balance. In some embodiments, a Zwitterionic group corresponds to a $C_{1-20}$ alkyl group substituted with at least one positively charged (cationic) substituent and at least one negatively charged (anionic) group, such that the overall charge of the Zwitterionic group is zero, and wherein the $C_{1-20}$ alkyl group is optionally further substituted with 1, 2, 3, 4, 5, or 6 substituents independently selected from halo, cyano, nitro, and $C_{1-4}$ haloalkyl, wherein 0, 1, 2, 3, 4, 5, or 6 carbon atoms of the $C_{1-20}$ alkyl group are individually replaced with O, S, C(O), C(O)O, NR', C(O)NR', SO, $SO_2$, $SO_2NR'$, wherein R' is H or $C_{1-6}$ alkyl, with the proviso that the replacement does not result in an unstable moiety (e.g., —O—O—, —O—S—, etc.).

Example Zwitterion groups comprise both a sulfonate group and a quaternary amine of formula $-NR_4^+$, wherein R is independently selected from $C_{1-6}$ alkyl, aryl, and arylalkyl. For example, the Zwitterionic group has Formula:

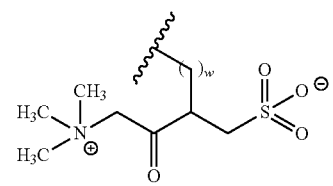

wherein w is 1, 2, 3, 4, 5, 6, 7, or 8.

In some embodiments, the Zwitterionic group has the Formula:

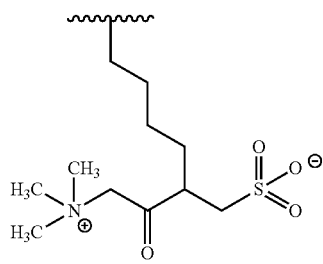

As used herein, the phrase "non-ionic oligomeric or polymeric solubilizing groups" refers to soluble polymers such as, for example, polyethylene glycol, polypropylene glycol, polyethylene oxide and propylene oxide copolymer, a carbohydrate, a dextran, polyacrylamide, and the like. The solubilizing group can be attached by any desired mode. The point of attachment can be, e.g., a carbon-carbon bond, a carbon-oxygen bond, or a nitrogen-carbon bond. The attachment group can be, e.g., an ester group, a carbonate group, a ether group, a sulfide group, an amino group, an alkylene group, an amide group, a carbonyl group, or a phosphate group.

Some examples of solubilizing groups include polyethylene glycols, such as $-(CH_2CH_2O)_a-H$, $-OC(=O)O(CH_2CH_2O)_aH$, $-OC(=O)O(CH_2CH_2O)_aCH_3$, $-O(CH_2CH_2O)_aCH_3$, and $-S(CH_2CH_2O)_aCH_3$, "a" being an integer between about 2 and about 250. In some embodiments, "a" is 4 to 12 or 5 to 10. In further embodiments, "a" is 6, 7, or 8. Other examples of solubilizing groups include dextrans such as $-OC(=O)O(dextran)$.

The solubilizing moiety can have an absolute molecular weight of from about 500 amu to about 100,000 amu, e.g., from about 1,000 amu to about 50,000 amu or from about 1,500 to about 25,000 amu.

In some embodiments, $R^9$ and $R^{10}$ are non-ionic oligomeric or polymeric solubilizing groups.

Further examples of solubilizing groups include: $-(CH_2)_c-(OCH_2CH_2)_d-OR^a$, wherein "c" is 0 to 6, "d" is 1 to 200, and $R^a$ is H or $C_{1-6}$ alkyl. In some embodiments, "c" is 1 to 4, "d" is 1 to 10, and $R^a$ is H. In some embodiments, "d" is 6 or 7.

See WO 2008/017074, U.S. Ser. No. 12/376,243 (filed Feb. 3, 2009), and U.S. Ser. No. 12/376,225 (filed Feb. 3, 2009), each of which is incorporated herein by reference in its entirety, for a further description of suitable non-ionic oligomeric or polymeric solubilizing groups, and method for incorporating them into dyes.

As used herein, "reactive linking group" (L') refers to any molecular entity having a molecular weight from about 50 to about 500 Da that is capable of conjugating with a targeting ligand (TL). In particular, the reactive linking group includes at least one reactive group selected from a carboxylic acid group or anhydride or ester thereof, as well as an isothiocyanate group. In some embodiments, the reactive linking group contains a carboxylic acid group.

In some embodiments, L' has the Formula:

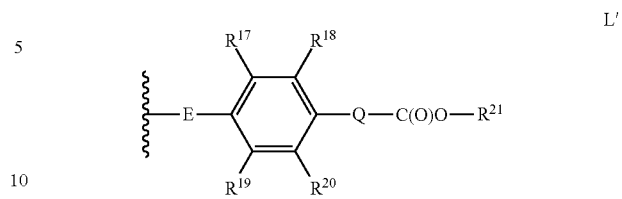

wherein:

E is absent, O or S;

Q is $(CH_2)_q$ or a non-ionic oligomeric or polymeric solubilizing moiety;

$R^{17}$, $R^{18}$, $R^{19}$, and $R^{20}$ are independently selected from H, an ionic group, a non-ionic oligomeric or polymeric solubilizing moiety, halo, cyano, nitro, $C_{1-4}$ alkyl, $C_{1-4}$ alkoxy, and $C_{1-4}$ haloalkyl;

$R^{21}$ is H or N-succinimidyl; and q is 0, 1, 2, 3, 4, 5, 6, 7, or 8.

In various embodiments, all or some of the following, or any combination of the following, may be true: E is absent or O; Q is $(CH_2)_q$; Q is $CH_2CH_2$; $R^{17}$, $R^{18}$, $R^{19}$, and $R^{20}$ are each H; $R^{21}$ is H; $R^{21}$ is N-succinimidyl; and q is 0.

The moiety $-C(O)O-R^{21}$ represents the reactive moiety of the reactive linking group that is capable of covalently attaching to a targeting ligand. Accordingly, $R^{21}$ can be H, to form the carboxy group which is reactive with amines or other nucleophiles. $R^{21}$ can also represent carboxyl activating substituents such as N-succidimidyl (NHS) which can facilitate conjugation.

Similarly, the "linking group" (L) is a divalent derivative of L' in the conjugates of the invention and has the same characteristics identified above except that the reactive group is covalently attached to the conjugated targeting ligand.

In some embodiments, L has the Formula:

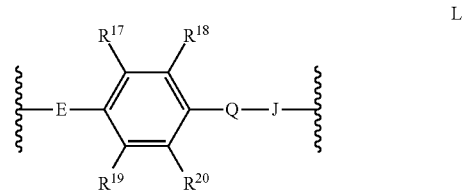

wherein:

E is absent, O or S;

Q is $(CH_2)_q$ or a non-ionic oligomeric or polymeric solubilizing moiety;

J is C(O), C(O)O, or C(O)NH;

$R^{17}$, $R^{18}$, $R^{19}$, and $R^{20}$ are independently selected from H, an ionic group, a non-ionic oligomeric or polymeric solubilizing moiety, halo, cyano, nitro, $C_{1-4}$ alkyl, $C_{1-4}$ alkoxy, and $C_{1-4}$ haloalkyl; and q is 0, 1, 2, 3, 4, 5, 6, 7, or 8.

In various embodiments, all or some of the following, or any combination of the following, may be true: E is absent or O; Q is $(CH_2)_q$; Q is $CH_2CH_2$; $R^{17}$, $R^{18}$, $R^{19}$, and $R^{20}$ are each H; q is 0; and J is C(O).

In some embodiments, L has the Formula:

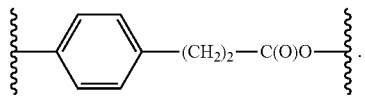

In some embodiments, L has the Formula:

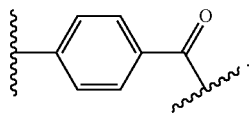 [SMILES: *C(=O)c1ccc(*)cc1]

See, Lee, H. et al. *J. Org. Chem.* (2006) 71(20), 7862-7865, incorporated herein by reference in its entirety.

As used herein, the term "methine" refers to a —CH= group. Similarly, the term "polymethine" refers to a chain of —CH= groups containing, for example, 2 to 20 carbon atoms. In some embodiments, the polymethine group has 3 to 13 carbon atoms. In further embodiments, the polymethine group has 3, 5, 7, 9, 11, or 13 carbon atoms. In yet further embodiments, the polymethine group is a heptamethine having 7 carbon atoms.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, sec-butyl, t-butyl), pentyl (e.g., n-pentyl, isopentyl, sec-pentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. In some embodiments, the aryl group is phenyl.

As used herein, "cycloalkyl" refers to non-aromatic cyclic hydrocarbon optionally including on or more unsaturations. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of cyclopentane, cyclopentene, cyclohexane, and the like. A cycloalkyl group containing a fused aromatic ring can be attached through any ring-forming atom including a ring-forming atom of the fused aromatic ring. In some embodiments, the cycloalkyl group is a 5-7 membered saturated cycloalkyl group.

As used herein, "carbocycle" or "carbocyclic" refers to an aryl or cycloalkyl group.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, any ring-forming N in a heteroaryl moiety can be substituted by oxo. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. In some embodiments, the heteroaryl group is a 5- or 6-membered heteroaryl ring.

As used herein, "heterocycloalkyl" refers to non-aromatic heterocycles having one or more ring-forming heteroatoms such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. The heterocycloalkyl group can be attached through a ring-forming carbon atom or a ring-forming heteroatom. The heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds. In some embodiments, the heterocycloalkyl group is a 5-, 6-, or 7-membered ring.

As used herein, "heterocycle" or "heterocyclic" refers to a heteroaryl group or heterocycloalkyl group.

As used herein, "halo" includes fluoro, chloro, bromo, and iodo.

As used herein, "arylalkyl" refers to alkyl substituted by aryl. An example arylalkyl group is benzyl.

As used herein, "alkoxy" refers to an —O-alkyl group. Example alkoxy groups include methoxy, ethoxy, propoxy (e.g., n-propoxy and isopropoxy), t-butoxy, and the like. At various places in the present specification, substituents are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Compounds of the invention can also include all isotopes of atoms occurring in the intermediates or final compounds. Isotopes include those atoms having the same atomic number but different mass numbers. For example, isotopes of hydrogen include tritium and deuterium.

The chemical substances represented herein by name, chemical formula, or structure are meant to include all stereoisomers, geometric isomers, tautomers, resonance structures, and isotopes of the same, unless otherwise specified.

The chemical substances described herein may be charged or include substituents with formal charges. When such chemical substances are represented as charged, it is understood that, unless otherwise specified, the charges are generally countered with an appropriate counterion. For example, chemical substances or functional groups having a charge of −1 are understood to be countered with an ion have a +1 charge. Suitable counterions with +1 charge include Na$^+$, K$^+$, tetraalkylammonium ions, and the like. Conversely chemical substances or functional groups having a charge of +1 are understood to be countered with an ion having a −1 charge. Suitable counterions with −1 charge include F—, Cl—, Br—, I—, perchlorate, acetate, trifluoroacetate, and the like.

Methods of Preparing Dyes and Conjugates

The present invention further provides methods for preparing dyes and conjugates suitable for the imaging methods described herein. In some embodiments, the methods include: (a) selecting a dye having peak absorption at about 500 nm to about 850 nm and peak fluorescent emission at about 550 nm to about 875 nm; (b) optionally modifying the dye to include a linking group; and (c) modifying the dye, and optionally the linking group, to include one or more ionic groups to achieve a solubility of the dye of at least about 10 µM in 10 mM HEPES solution at pH 7.4; wherein the one or more ionic groups are selected so that the net charge of the dye is +1, 0, or −1, and wherein the signal-to-background ratio of fluorescent emission detected from the dye compound while imaging is at least about 1.1.

The present invention further provides methods of preparing a conjugate for imaging tissue or cells, wherein the conjugate includes a dye and a targeting ligand. These methods include: (a) selecting a dye having peak absorption at about 500 nm to about 850 nm and peak fluorescent emission at about 550 nm to about 875 nm; (b) optionally modifying the dye to include a linking group; (c) modifying the dye and optionally the linking group to include one or more ionic groups to achieve a solubility of at least about 10 µM in 10 mM HEPES solution at pH 7.4; and (d) conjugating the targeting ligand to the dye optionally through the linking group to form the conjugate, wherein the targeting ligand and the one or more ionic groups are selected so that the net charge of the conjugate is +1, 0, or −1, and wherein the signal-to-background ratio of fluorescent emission detected from the conjugate while imaging is at least about 1.1

The dyes described herein can be synthesized according to standard procedures known in the art of organic chemistry. Numerous preparation of Cyanine dyes have been published. Accordingly, the dyes of the invention can be prepared according to any of the known literature methods. See, for example, Mojzych, M. et al. "Synthesis of Cyanine Dyes" Top. Heterocycl. Chem. (2008) 14:1-9; Sysmex Journal International (1999), Vol. 9, No. 2, pg 185 (appendix); Strekowski, L. et al. Synthetic Communications (1992), 22(17), 2593-2598; Strekowski, L. et al. J. Org. Chem. (1992) 57, 4578-4580; Narayanan, N. et al. J. Org. Chem. (1995), 60(8), 2391-2395; Makin, S. M. et al. Journal of Organic. Chemistry of the USSR (1977) 13 (6), part 1, 1093-1096; Lee, H. et al. J. Org. Chem. (2006) 71, 7862-7865, WO 2009/006443, WO 2008/015415, WO 2007/136996, WO 2007/005222, WO 2003/082988, WO 2001/090253, U.S. Ser. No. 12/376,243 (filed Feb. 3, 2009), and U.S. Ser. No. 12/376,225 (filed Feb. 3, 2009), each of which is incorporated herein by reference in its entirety.

The dyes, conjugates, and imaging agents can be isolated as salts, acids, bases, or combinations thereof. For example, dyes, conjugates, and imaging agents having multiple charged substituents can be isolated by introducing counterions and/or protons sufficient to counter the charges of the various substituents normally present in neutral pH so that the dye, conjugate, or imaging agent can be isolated, for example, as a solid substance.

Applications, Properties, and Compositions

The conjugates described herein can be used for, e.g., optical tomographic, endoscopic, photoacoustic, and sonofluorescent applications for the detection, imaging, and treatment of tumors and other abnormalities. The conjugates can also be used for localized therapy. This can be accomplished, e.g., by attaching a porphyrin or other photodynamic therapy agent to a conjugate; directing the conjugates to a desired target site, or allowing the conjugates to accumulate selectively in the target site; shining light of an appropriate wavelength to activate the agent. Thus, the new conjugates can be used to detect, image, and treat a section of tissue, e.g., a tumor.

In addition, the conjugates can be used to detect the presence of tumors and other abnormalities by monitoring the blood clearance profile of the conjugates, for laser assisted guided surgery for the detection of small micrometastases of, e.g., somatostatin subtype 2 (SST-2) positive tumors, and for diagnosis of atherosclerotic plaques and blood clots.

The conjugates can be formulated into diagnostic and therapeutic compositions for enteral or parenteral administration. Generally, these compositions contain an effective amount of the conjugate, along with conventional pharmaceutical carriers and excipients appropriate for the type of administration contemplated. For example, parenteral formulations include the dye or dye conjugate in a sterile aqueous solution or suspension. Parenteral compositions can be injected directly into a subject at a desired site, or mixed with a large volume parenteral composition for systemic administration. Such solutions can also contain pharmaceutically acceptable buffers and, optionally, electrolytes, such as sodium chloride.

Formulations for enteral administration, in general, can contain liquids, which include an effective amount of the desired dye or dye conjugate in aqueous solution or suspension. Such enteral compositions can optionally include buffers, surfactants, and thixotropic agents. Compositions for oral administration can also contain flavoring agents, and other ingredients for enhancing their organoleptic qualities.

Generally, the diagnostic compositions are administered in doses effective to achieve the desired signal strength to enable detection. Such doses can vary, depending upon the particular dye or dye conjugate employed, the organs or tissues to be imaged, and the imaging equipment being used. For example, Zeheer et al., *Nature Biotechnology*, 19, 1148-1154 (2001) uses 0.1 µmol/kg as a dose for IRDye78 conjugates in vivo. The diagnostic compositions can be administered to a patient systemically or locally to the organ or tissue to be imaged, and then the patient is subjected to the imaging procedure.

Generally, the conjugates or dye compounds absorb and emit light in the visible and infrared region of the electromagnetic spectrum, e.g., they can emit green, yellow, orange, red light, or near infrared light ("NIR").

In some embodiments, the dyes emit and/or absorb radiation having a wavelength from about 300 nm to about 1000 nm, e.g., from about 400 nm to about 900 nm, or from about 450 nm to about 850 nm.

In some embodiments the conjugates and dye compounds have a maximum excitation and/or a maximum emission, measured in 10 mM HEPES solution, pH 7.4, of from about 525 nm to about 875 nm, e.g., from about 550 nm to about 825 nm, or from about 550 nm to about 800 nm.

The invention will be described in greater detail by way of specific examples. The following examples are offered for illustrative purposes, and are not intended to limit the invention or claims in any manner. A variety of noncritical parameters in these examples can be changed or modified to yield essentially the same results.

EXAMPLES

Example 1

Dyes

FIG. 1 depicts certain dyes that can be used in the imaging methods of the invention. Note that for molecules ZW−3, ZW−1, ZW+1, ZW+3, and ZW+5, a targeting ligand would have to be introduced having a +3, +1, −1, −3, and −5 charge, respectively, to achieve neutrality.

Example 2

Preparation of Dye ZW+1

Figure 2:
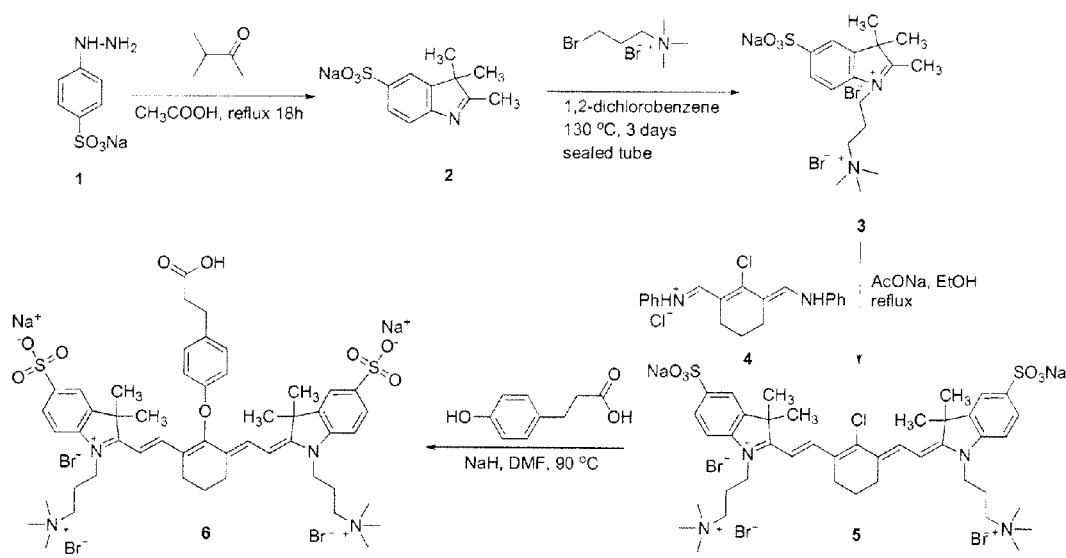
FIG. 2 is a schematic of the synthesis of dye molecule ZW+1 (MM-19).

Dye ZW+1 (see FIG. 1) was made according to the synthetic procedure depicted in FIG. 2. Sodium 4-hydrazinylbenzenesulfonate (1) was reacted with 3-methylbutan-2-one to form the 2,3,3-trimethyl-3H-indole derivative (2). The indole nitrogen was then capped by reaction with 3-bromo-N,N,N-trimethylpropan-1-aminium bromide, and the product (3) reacted with the 2-chloro-3-((phenylamino)methylene)cyclohex-1-enyl)methylene)benzenaminium compound (4) to yield the Cyanine dye (5). A linking group was attached by reaction of (5) with 3-(4-hydroxyphenyl)propanoic acid to form the ZW+1 dye (6). See also Mojzych, M. et al. "Synthesis of Cyanine Dyes" Top. Heterocycl. Chem. (2008) 14:1-9; *Sysmex Journal International* (1999), Vol. 9, No. 2, pg 185 (appendix); Strekowski, L. et al. *Synthetic communications* (1992), 22(17), 2593-2598; Strekowski, L. et al. *J. Org. Chem.* (1992) 57, 4578-4580; and Makin, S. M. et al. *Journal of Organic Chemistry of the USSR* (1977) 13 (6), part 1, 1093-1096, each of which is incorporated herein by reference in its entirety.

Example 3

Preparation of Dye ZW+5

Figure 3:
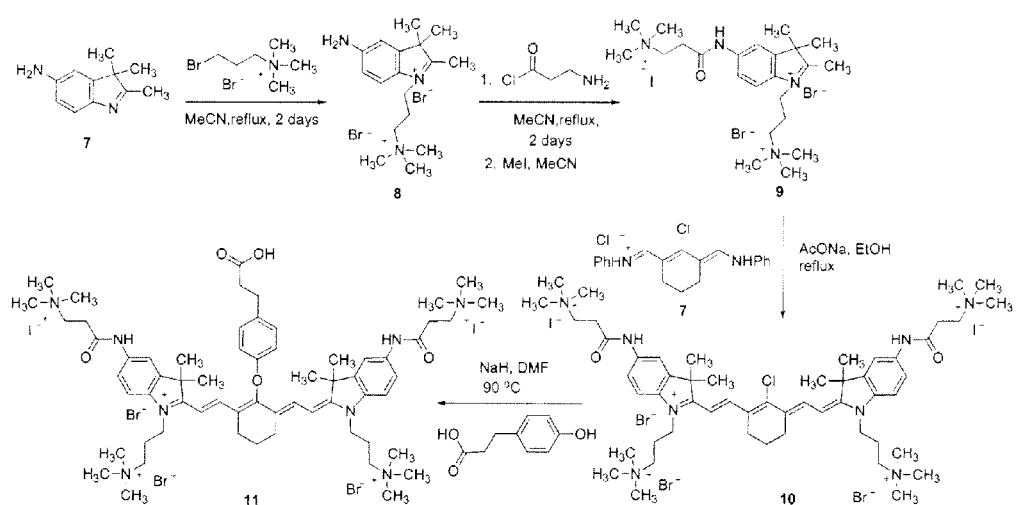
FIG. 3 is a schematic of the synthesis of dye molecule ZW+5.

Dye ZW+5 (see FIG. 1) can be made according to the synthetic procedure depicted in FIG. 3. The first step involves alkylation of indolenine 7. The resultant quaternary salt 8 can be allowed to react with 3-aminopropanoyl chloride (in the form of an ammonium salt to protect the amino group). Then the terminal amino group can be quaternized with excess of methyl iodide to give the bis-quaternary salt 9. The subsequent steps 9→10→11 are analogous to the synthesis described in Example 2 above. Ion exchange can be used to prepare final products with a single counter anion such as chloride or bromide.

The presence of a quaternary ammonium cation close to the aromatic ring may inhibit formation of the final dye. Accordingly, a short spacer between the aromatic ring and the ammonium group of ZW+5 can be introduced.

Purification can be accomplished through silica gel chromatography or reverse-phase chromatography under both high and low-pressure conditions. Size exclusion chromatography may also be useful.

Example 4

Characterization of Dyes

After purification to homogeneity, optical properties of the dyes can be measured in 100% calf serum. Absorbance spectrometry (200 to 870 nm) can be performed using a USB2000 fiber optic spectrometer and CHEM2000-UV-VIS light source with cuvette holder (Ocean Optics, Dunedin, Fla.). Fluorescence spectrometry (200 to 1100 nm) can be performed using a HR2000 fiber optic spectrometer, CUV-ALL-UV 4-way cuvette holder (Ocean Optics), and a 250 mW 770 nm laser diode (Electro Optical Components, Santa Rosa, Calif.). Quantum yield can be measured under conditions of matched absorbance and 770 nm laser excitation, using ICG in DMSO (QY=13%) as the calibration standard.

Example 5

Preparation of Charge-Balanced Conjugates

Prior to in vivo testing, dyes are converted into "charge-balanced" imaging agents with net charge=0, so that they recapitulate the net charge after conjugation to a targeting ligand. Purely anionic or cationic charge can be introduced through a free carboxylic acid on the linking group of the dyes using, for example, amino-adamantane derivatives, described in detail previously (Maison, W., J. V. Frangioni, and N. Pannier, Synthesis of rigid multivalent scaffolds based on adamantane. Org Lett, 2004. 6: 4567-9; Nasr, K., N. Pannier, J. V. Frangioni, and W. Maison, *Rigid Multivalent Scaffolds Based on Adamantane*. J Org Chem, 2008; and U.S. Pat. App. Pub. No. 2006/0063834, each of which is incorporated herein by reference.

Figure 9:
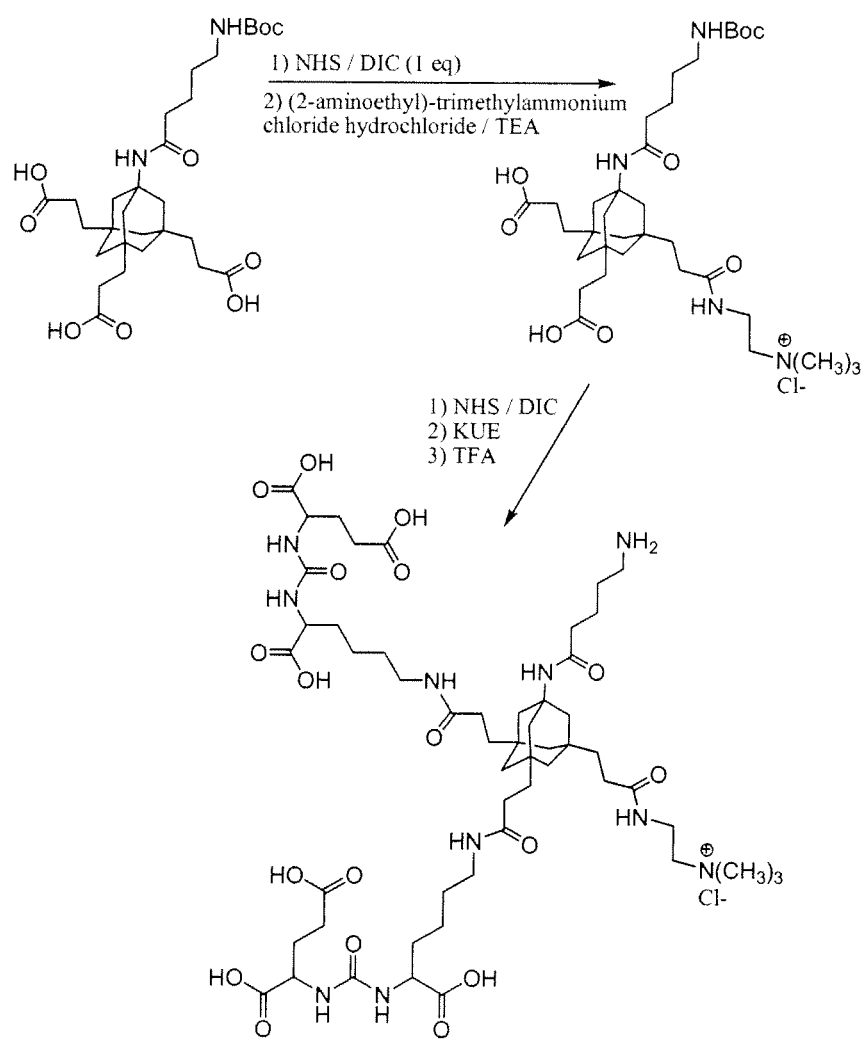
FIG. 9 is a representation of the preparation of an example adamantane-based targeting ligand containing an ionic group for charge-balancing and moieties that selectively bind to PSMA.

Briefly, to introduce cationic "balancing" groups, one, two or three of the available bridgehead carboxylic acid groups of amino-tri-carboxy-adamantane (ATCA) (see FIG. 9) can be conjugated to either (2-aminoethyl)trimethylammonium chloride or 2,2'-iminobis(N,N,N-trimethylethanaminium chloride), and any remaining carboxylic acids blocked with ethanolamine, to create molecules with +1, +2, +3, +4, +5, and +6 charge. Similarly, to create balancing groups with −1, −2, −3, −4, −5, and −6 charge, the three bridgehead carboxylic acids of ATCA will be either uncapped (i.e., remaining carboxylic acids), capped with ethanolamine, or conjugated to glutamate. The appropriate balancing group can be conjugated covalently to each dye to produce a final conjugate, having net charge=0, prior to in vivo characterization.

Example 6

Imaging of Organisms

The FLARE™ Image-Guided Surgery System is a continuous-wave (CW) intraoperative imaging system that is capable of simultaneous, real-time acquisition and display of color video (i.e., surgical anatomy) and two channels of invisible NIR fluorescent (700 nm and 800 nm) light. Details of the theory, engineering, and operation of the imaging system has been described in detail previously. See, Tanaka, E., H. S. Choi, H. Fujii, M. G. Bawendi, and J. V. Frangioni, *Image-guided oncologic surgery using invisible light: completed pre-clinical development for sentinel lymph node mapping.* Ann Surg Oncol, 2006. 13: 1671-81; De Grand, A. M. and J. V. Frangioni, *An operational near-infrared fluorescence imaging system prototype for large animal surgery.* Technol Cancer Res Treat, 2003. 2: 553-562; and Nakayama, A., F. del Monte, R. J. Hajjar, and J. V. Frangioni, *Functional near-infrared fluorescence imaging for cardiac surgery and targeted gene therapy.* Molecular Imaging, 2002. 1: 365-377, each of which is incorporated herein by reference.

Specifications for the FLARE™ Image-Guided Surgery System is provided in Table 1 below.

TABLE 1

FLARE ™ NIR Fluorescence Imaging System Specifications

| Category | Specification | Description |
| --- | --- | --- |
| Physical | Size | Mobile Cart: 32" W × 32" D × 41.4" H; Mast Height: 82" |
| | Weight | 675 lbs, including all electronics |
| | Arm | 6-degree-of-freedom; Reach: 43"-70" from floor, 50.7" from cart |
| Electrical | Voltage and Plug | 120 V AC, 60 Hz; single NEMA 5-15 120 V/15 A AC plug |
| | Current | 15 A max |
| | Grounding | Isolation transformer for all components; redundant chassis grounding |
| | Leakage Current | <300 µA (per AAMI/IEC #60601) |
| Sterility | Shield | Disposable acrylic shield with ≥95% transmission |
| | Drape | Disposable, custom-fit plastic drape bonded to shield |
| Light Source | Housing | Anodized aluminum with secondary 400 W cooling plate |
| | Elements | Custom 25 mm circular LED arrays w/ integrated linear drivers |
| | Electronics | Custom passive and active boards with embedded controller |
| | Fluence Rates | 40,000 lx white light (400-650 nm), 4 mW/cm$^2$ of 700 nm (656-678 nm) excitation light, 14 mW/cm$^2$ of 800 nm (745-779 nm) excitation light |
| Optics | Working Distance | 18" from surface of patient |
| | Field-of-View | 2.2 W × 1.7 H cm to 15 W × 11.3 cm (adjustable zoom) |
| | Emission/Reflectance Channels | Color Video (400-650 nm), 700 nm fluorescence (689-725 nm), 800 nm fluorescence (800-848 nm), all with simultaneous acquisition |
| | Pixel Resolution | 640 × 480 for each camera |
| | System Resolution | 125 × 125 µm (x, y) to 625 × 625 µm (x, y) |
| | Display Refresh | Up to 15 Hz simultaneous acquisition on all 3 camera |
| | NIR Exposure Time | Adjustable from 100 µsec to 8 sec |
| Hands-Free Control | Optics | Automatic zoom/focus |
| | | 6-pedal footswitch |
| Monitors | Number | 2 cart-mounted 20" for operator; 1 satellite 20" on stand for surgeon |

Example 7

In vivo Characterization of Dyes and Conjugates

For in vivo characterization, 40 pmol/g (average 10 nmol) of each dye or conjugate can be injected IV into 250 g Sprague-Dawley rats whose major viscera are surgically exposed. The FLARE™ imaging system can be set to a 760 nm excitation fluence rate of 5 mW/cm2. Simultaneous color video and NIR fluorescence (800 nm) images can be acquired pre-injection, every 1 sec for the first 20 sec then every 1 min for 2 h. Camera acquisition can be held constant (typically 100 msec) and chosen to ensure that all intensity measurements are within the linear range of the 12-bit Orca-AG (Hamamatsu) NIR camera. Blood can be sampled at 0, 1, 2, 5, 10, 15, 30, 60, and 120 min via tail vein. Intensity-time curves for all major organs and tissues can be quantified. The peak fluorescence intensity and time can be determined for each tissue/organ, along with the intensity in each at 1 h post-injection. The experiment can then be repeated in pigs, with measurement of NIR fluorescent intensity of skin and all internal tissues and organs. A statistical justification for rat and pig usage can be found in Vertebrate Animals.

Example 8

In vitro Optical and Stability Properties of Dyes

Figure 4:
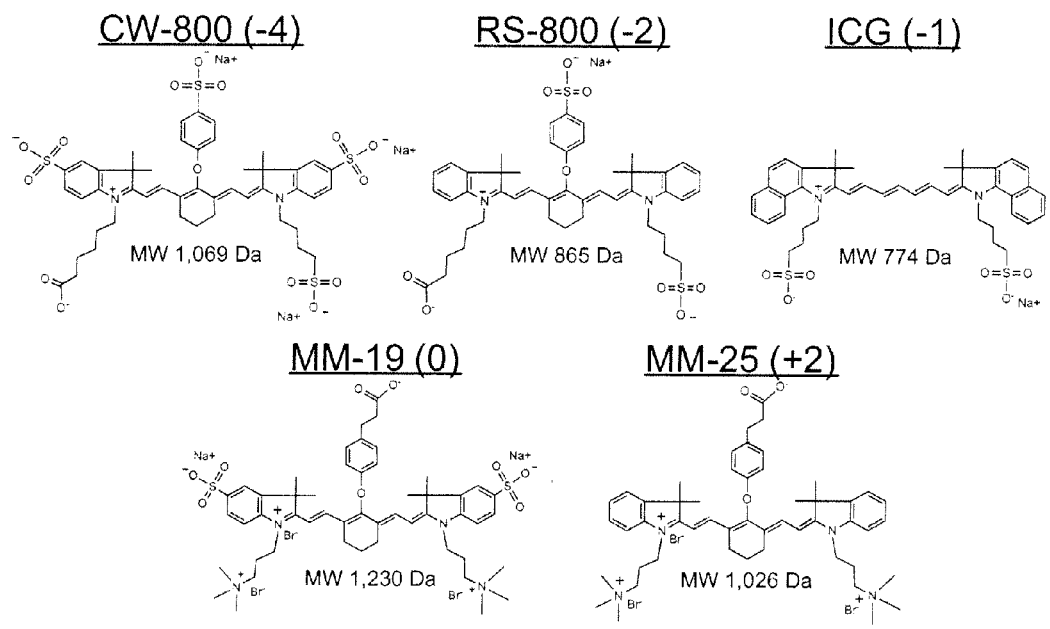
FIG. 4 is a representation of five dye molecules, the properties of which were compared in vitro and in vivo.

Five heptamethine indocyanine dyes, ranging in net charge from −4 to +2 are shown in FIG. 4 and were characterized with respect to their optical properties and stability in vitro. Commercial NIR fluorophores, such as IRDye™ 800-RS (RS-800), IRDye800-CW (CW-800), Cy5.5, and Cy7 have various degrees of sulfonation in order to achieve aqueous solubility. NIR fluorophore MM-25 (+2 net charge) was prepared by employing quaternary ammonium cations (quats). MM-19 was synthesized by employing both sulfonate groups and quats, following the synthetic scheme outlined in FIG. 2 (see Example 2). Note that MM-19 (ZW+1, see FIG. 1) has a net charge of zero.

Table 2 below summarizes the optical and stability properties of each of these dyes in 100% calf serum (supplemented with 50 mM HEPES, pH 7.4).

TABLE 2

Optical Properties of Variously Charged NIR Fluorophores in 100% serum.

| NIR Fluorophore | MW | Net Charge (Individual charges) | Peak Absorbance | Extinction Coefficient ($M^{-1}cm^{-1}$) | Peak Emission | QY | Stability at 4 h, 37° C. |
|---|---|---|---|---|---|---|---|
| CW-800 | 1,069 | −4 (−5, +1) | 786 nm | 237,000 | 801 nm | 14.2% | 95% |
| RS-800 | 865 | −2 (−3, +1) | 784 nm | 240,000 | 800 nm | 16.9% | 97% |
| ICG | 774 | −1 (−2, +1) | 807 nm | 121,000 | 822 nm | 9.3% | 96% |
| MM-19 | 1,230 | 0 (−3, +3) | 773 nm | 249,000 | 790 nm | 13.7% | 95% |
| MM-25 | 1,026 | +2 (+3, −1) | 772 nm | 309,000 | 790 nm | 16.1% | 97% |

Example 9

Comparative in Vivo Behavior of Dyes

Figure 5:
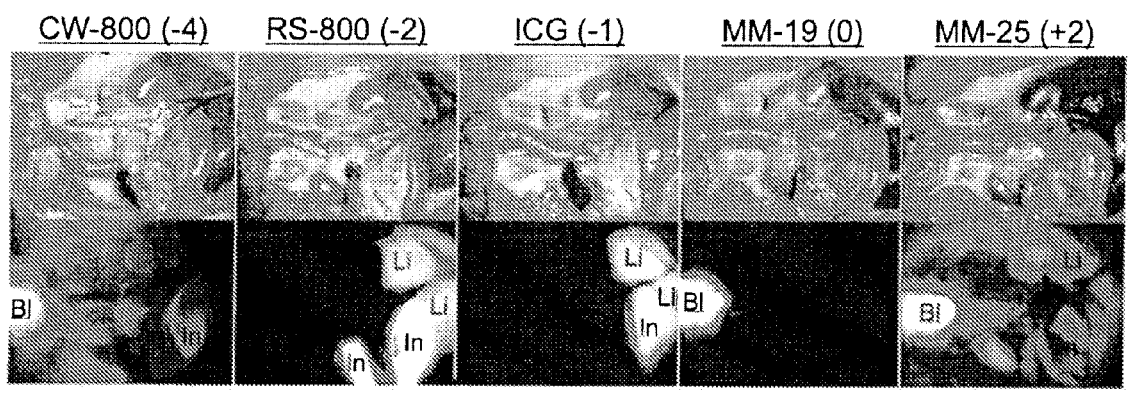
FIG. 5 is a representation of experimental results relating to in vivo biodistribution and clearance of the dye molecules of FIG. 4 in a rat model.

While the in vitro optical and stability properties for the five tested dyes in Example 8 were similar, the in vivo behavior of these dyes was shown to be dramatically different. Results are shown in FIG. 5. The dyes were injected IV into rats at a dose of 40 pmol/g (10 nmol). Shown in FIG. 5 are the color video (top row) and 800 nm NIR fluorescence (bottom row) images of all major organs and tissues, surgically exposed. Excitation fluence rate was 5 mW/cm2. Camera integration time was 200 msec. All NIR fluorescence images have identical normalizations. Bl=bladder. Li=Liver. In=Intestines.

As can be seen in FIG. 5, the dye with net charge of 0 (MM-19) outperformed the other dyes. The dyes with −1 (ICG) or −2 (RS-800) net charge and having a high "hydrophobic moment" (i.e., one half of molecule is highly hydrophobic and the other half is hydrophilic), resulted in undesirable rapid uptake by the liver (i.e., short blood half-life) and eventual excretion into bile. The dye with −4 net charge (CW-800) was cleared equally by liver and kidneys, resulting in high intestinal signal, but also demonstrated relatively high retention in skin and other major tissues and organs. The dye with +2 net charge (MM-25) was cleared by kidney more than liver, however, non-specific uptake in organs and tissue was relatively high. Finally, MM-19, which has a net charge of zero, demonstrated rapid equilibration between intravascular and extravascular spaces, no measurable liver uptake, rapid renal excretion into urine, and extremely low background retention in normal tissues and organs.

Figure 6:
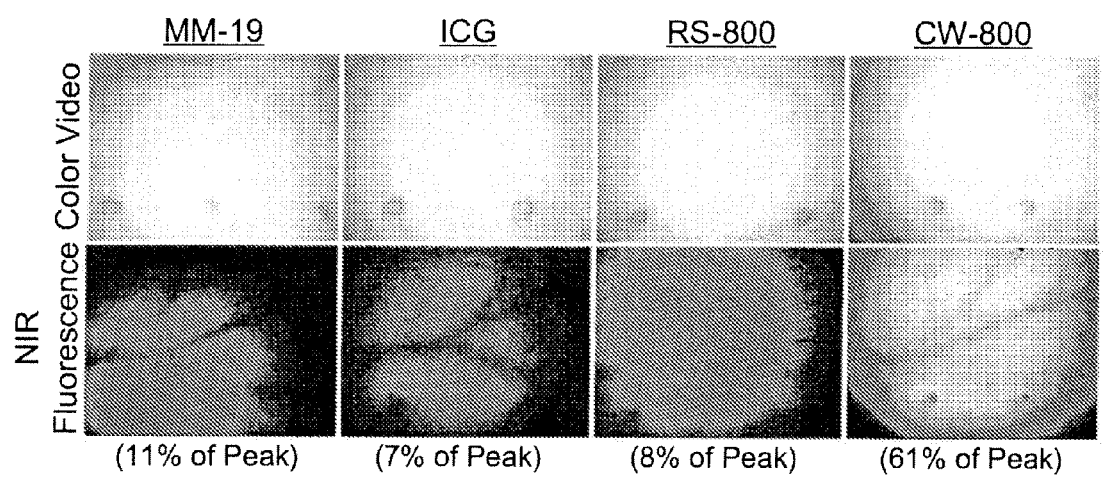
FIG. 6 is a representation of experimental results relating to in vivo biodistribution and clearance of the dye molecules of FIG. 4 in a pig model.

These results were confirmed in pig (FIG. 6). All dyes were injected IV into pigs at a dose of 40 pmol/g (1.6 pawl). Shown in FIG. 6 are the color video and NIR fluorescence (800 nm) images of skin, along with the measured SBR of skin 1 h post-injection. Excitation fluence rate was 5 mW/cm2. Camera integration time was 200 msec. All NIR fluorescence images had identical normalizations. Even after only 1 h of clearance, MM-19 signal in skin was only 11% of peak fluorescence (FIG. 6), and no non-specific uptake was seen in any other tissues and organs. This is in contrast to ICG, RS-800, and CW-800, which resulted in very high uptake in pig liver and intestines. Blood half-lives of CW-800, RS-800, ICG, MM-19, and MM-25 were 30.6, 6.5, 4.6, 13.4, and 44.0 min, respectively.

Example 10

Comparative in Vivo Behavior of Conjugates

Figure 7:
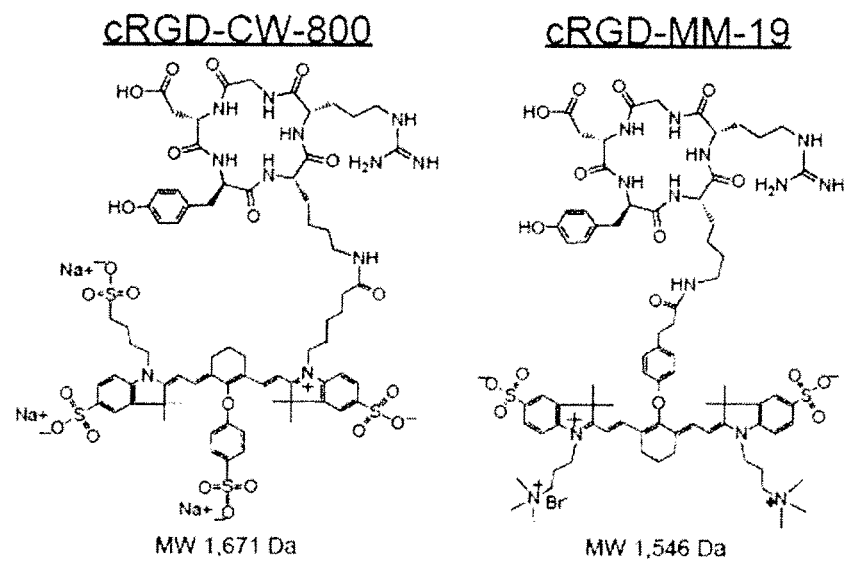
FIG. 7 is a representation of two different dyes conjugated to the targeting ligand cRGD.

Dyes CW-800 (see FIG. 4) with net charge −4 and MM-19 (see FIG. 4) with net charge of 0 were conjugated with cRGD, a specific binder to $\alpha_v\beta_3$ integrin. See FIG. 7 for structures of the conjugates.

Athymic nu/nu mice with integrin $\alpha_v\beta_3$-expressing tumors on the left flank (T+; arrows) and integrin $\alpha_v\beta_3$-negative tumors (T−; arrowheads) on the right flank were used in this experiment. Shown are color video (top row) and 800 NIR fluorescence images (bottom row) at 0 and 4 h after IV injection of 40 pmol/g (1 nmol) of cRGD-CW-800 (left) and cRGD-MM-19 (right)

Figure 8:
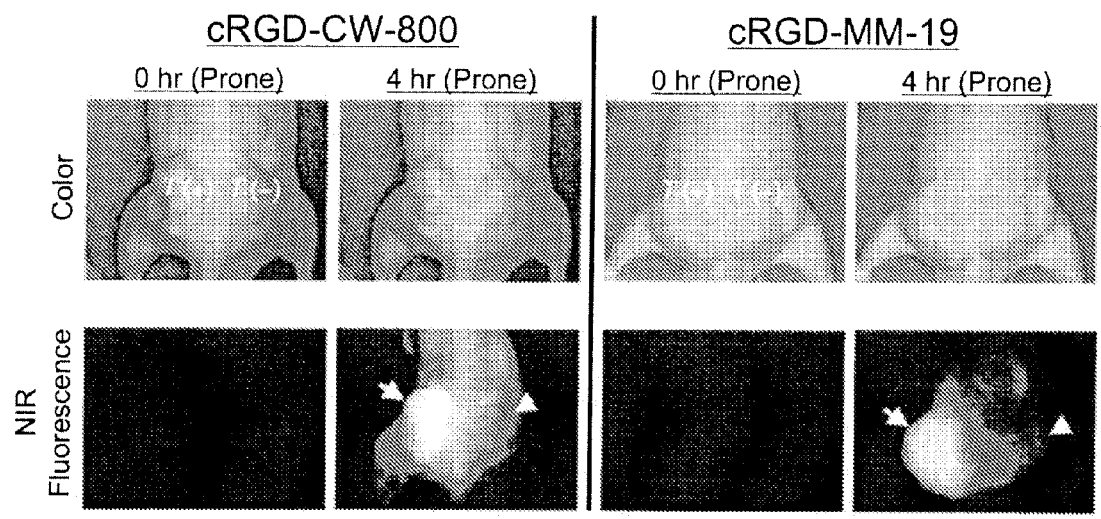
FIG. 8 is a representation of in vivo experimental results in rat tumor models for the two conjugates of FIG. 7.

Even though net charge on the cRGD-MM-19 conjugate was +1 due to the indole nitrogen, the results were clear that this conjugate had superior imaging properties. After IV injection of identical doses of cRGD-MM-19 and cRGD-CW-800, the MM-19 based conjugate had a much higher tumor-to-background ratio (TBR) at all time points and exhibited rapid renal clearance (see FIG. 8). The CW-800 based conjugate (net charge −3) had very high non-specific uptake in skin, muscle, and bone (FIG. 8). At 4 h post-injection, cRGD-CW-800 had a TBR of 5.0 and cRGD-MM-19 had a TBR of 17.2, corresponding to a 3.4-fold improvement in TBR.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of imaging tissue or cells, the method comprising:
    (a) contacting the tissue or cells with an imaging agent comprising a dye;
    (b) irradiating the tissue or cells at a wavelength absorbed by the dye;
    (c) detecting an optical signal from the irradiated tissue or cells, wherein the signal-to-background ratio of the detected optical signal is at least about 1.1, thereby imaging the tissue or cells;
wherein the dye has the formula X:

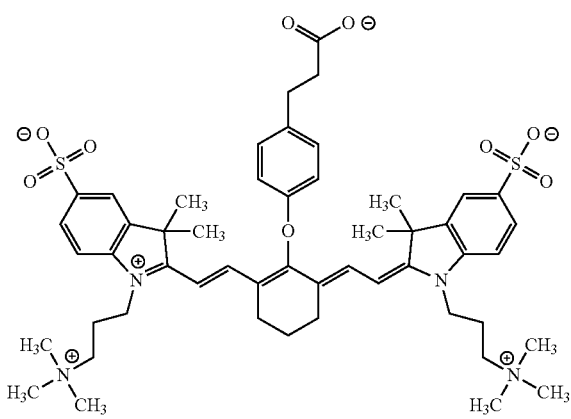

X or an ester thereof, which permits covalent conjugation of the fluorophore to targeting ligands.

2. A dye, having the formula X:

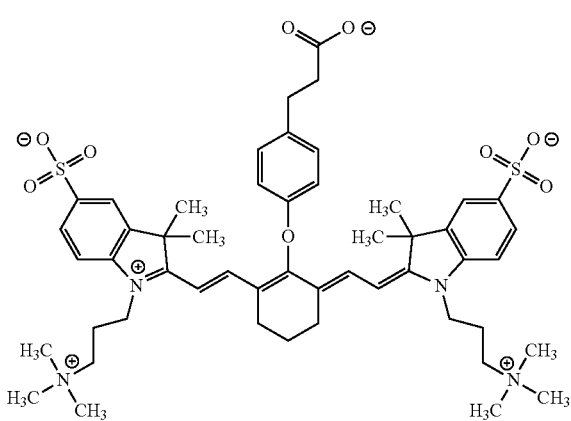

X or an ester, an acid, a salt, or a combination of an acid or a salt, thereof, which permits covalent conjugation of the fluorophore to targeting ligands.

3. The dye of claim 2, wherein the ester is a N-hydroxysuccinimide ester.

4. The dye of claim 2, wherein the dye is a salt, an acid, or a combination of a salt and an acid.

5. A method of imaging tissue or cells, the method comprising:
    (a) contacting the tissue or cells with an imaging agent comprising a conjugate of a dye;
    (b) irradiating the tissue or cells at a wavelength absorbed by the conjugate;
    (c) detecting an optical signal from the irradiated tissue or cells, wherein the signal-to-background ratio of the detected optical signal is at least about 1.1, thereby imaging the tissue or cells;
wherein the conjugate has the formula VII:

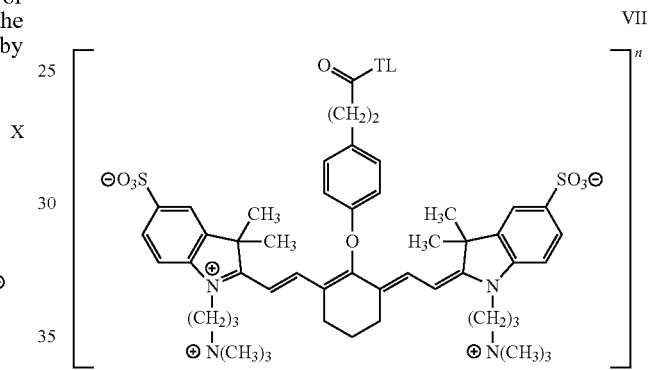

VII

Wherein n is 0, +1, or −1; and

TL is a targeting ligand.

6. A conjugate having the formula VII:

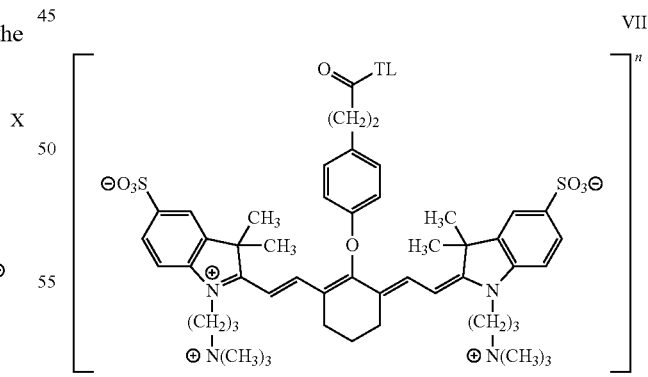

VII

Wherein n is 0, +1, or −1; and

TL is a targeting ligand.

7. An imaging agent comprising the conjugate of claim 6 which is characterized as having detectable fluorescence with a signal-to-background ratio of at least about 1.1.

* * * * *